(12) United States Patent
Akireddy et al.

(10) Patent No.: US 8,153,821 B2
(45) Date of Patent: Apr. 10, 2012

(54) COMPOUNDS

(75) Inventors: Srinivasa Rao Akireddy, Winston-Salem, NC (US); Balwinder Singh Bhatti, Winston-Salem, NC (US); Timothy J. Cuthbertson, Winston-Salem, NC (US); Craig Harrison Miller, Winston-Salem, NC (US); Joseph Pike Mitchener, Jr., Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 13/130,954

(22) PCT Filed: Nov. 30, 2009

(86) PCT No.: PCT/US2009/066083
§ 371 (c)(1),
(2), (4) Date: Jul. 20, 2011

(87) PCT Pub. No.: WO2010/065447
PCT Pub. Date: Jun. 10, 2007

(65) Prior Publication Data
US 2011/0269975 A1    Nov. 3, 2011

Related U.S. Application Data

(60) Provisional application No. 61/118,885, filed on Dec. 1, 2008.

(51) Int. Cl.
C07D 207/12    (2006.01)
A61K 31/40     (2006.01)
(52) U.S. Cl. .................................... 548/531; 514/423
(58) Field of Classification Search .................. None
See application file for complete search history.

(56) References Cited

U.S. PATENT DOCUMENTS

| | | | |
|---|---|---|---|
| 5,583,140 | A | 12/1996 | Bencherif |
| 5,597,919 | A | 1/1997 | Dull |
| 5,604,231 | A | 2/1997 | Smith |
| 5,852,041 | A | 12/1998 | Cosford |
| 6,310,043 | B1 | 10/2001 | Bundle |
| 6,846,835 | B2 * | 1/2005 | Ogino et al. ............ 514/317 |
| 2001/0056084 | A1 | 12/2001 | Allgeier et al. |

FOREIGN PATENT DOCUMENTS

| | | |
|---|---|---|
| JP | WO 96/40682 | 12/1996 |
| WO | WO 94/08992 | 4/1994 |
| WO | WO 96/31475 | 10/1996 |
| WO | WO 98/25619 | 6/1998 |
| WO | WO 2004/078752 | 9/2004 |

OTHER PUBLICATIONS

Arneric, S., et al., "Perclinical Pharmacology of ABT-418: A Prototypical Cholinergic Channel Activator for the Potential Treatment of Alzheimer's Disease," CNS Drug Rev. 1(1):1-26 (1995).
Arneric, S., et al., "Cholinergic channel modulators as a novel therapeutic strategy for Alzheimer's disease," Exp. Opin. Invest. Drugs 5(1): 79-100(1996).
Bannon, et al., "Broad-Spectrum, Non-Opioid Analgesic Activity by Selective Modulation of Neuronai Nicotinic Acetylcholine Receptors," Science 279: 77-80 (1998).
Bencherif, M, and R.J. Lukas, "Ligand Binding and Functional Characterization of Muscarinic Acetylcholine Receptors on the TE671/ RD Human Cell Line," J. Pharmacol. Exp. Ther, 257(3): 946-953 (1991).
Bencherif, M., et al., "RJR-2403: A Nicotinic Agonist with CNS Selectivity I: In VitroCharacterization," J. Pharmacol. Exper. Therapeutics 279(3): 1413-1421 (1996).
Bencherif M. and R.J. Lukas, "Differential Regulation of Nicotinic Acetylcholine Receptor Expression by Human TE671/RD Cells Following Second Messenger Modulation and Sodium Butyrate Treatments," Mol Cell Neurosci., 2(1): 52-65 (1991).
Breining, S. et al, "Neuronal Nicotinic Acetylcholine Receptor Modulators: Recent Advances and Therapeutic Potential," Annual Reports in Medicinal Chemistry, 40: 3-16(2005).
Cheng, Yung-Chi, and W.H. Prusoff, "Relationship Between the inhibition Constant ($K_1$) and the Concentration of Inhibitor which Causes 50 Per Cent inhibition ($I_{50}$) of an Enzymatic Reaction," Biochem. Pharmacol. 22(23): 3099-3108 (1973).
Chiari, A., et al., "Sex Differences in Cholinergic Analgesia I: A Supplemental Nicotinic Mechanism in Normal Females," Anesthesiology 91(5): 1447-1454 (1999).
Damaj, M.I., et al., "Antinociceptive and Pharmacological Effects of Metanicotine, a Selective Nicotinic Agonist," J. Pharmacol. Exp. Ther., 291(1): 390-398 (1999).
Davies, Andrew R.L., et al., "Characterisation of the binding of [$^3$H]methyllycaconitine: a new radioligand for labeling α7-type neuronal nicotinic acetylcholine receptors," Neuropharmacol. 38:679-690 (1999).
Hogg, R.C. and D. Bertrand, "Nicotinic Acetylcholine Receptors as Drug Targets," Current Drug Targets; CNS Neurol. Disord., 3: 123-130 (2004).
Holladay, et al., "Neuronal Nicotinic Acetylcholine Receptors as Targets for Drug Discovery," J. Med. Chem., 40(26): 4169-4194 (1997).
Lavand'homme, P., and J.C. Eisenach, "Sex Differences in Cholinergic Analgesia II: Differing Mechanisms in Two Models of Allodynia," Anesthesiology 91(5):1455-1461 (1999).
Lippielio, P.M., et al., "RJR-2403: A Nicotinic Agonist with CNS Selectivity II. In Vivo Characterization," J. P. E. T. 279(3): 1422-1429 (1996).
Lowry, et AL., "Protein Measurement with the Folin Phenol Reagent,"J. Biol. Chem. 193: 265-275 (1951).

(Continued)

Primary Examiner — Yong Chu
Assistant Examiner — Michael Barker
(74) Attorney, Agent, or Firm — Amy H. Fix

(57) ABSTRACT

The present invention related to compounds that bind to and modulate the activity of neuronal nicotinic acetylcholine receptors, to novel salts thereof, to processes for preparing these compounds, to pharmaceutical compositions containing these compounds, and to methods of using these compounds for treating a wide variety of conditions and disorders, including those associated with dysfunction of the central nervous system (CNS).

5 Claims, 3 Drawing Sheets

OTHER PUBLICATIONS

Lukas, RJ, and M.J. Cullen, "An Isotopic Rubidium Ion Efflux Assay for the Functional Characterization of Nicotinic Acetylcholine Receptors on Clonal Cell Lines," *Anal. Biochem.* 175(1): 212-218 (1988).

Lukas, R.J., "Pharmacological Distinctions between Functional Nicotinic Acetylcholine Receptors on the PC12 Rat Pheochromocytoma and the TE671 Human Medulloblastoma," *J. Pharmacol. Exp. Ther.* 251(1): 175-182 (1989).

Luine, V.N., et al., "Chromaprolne and Chromaperidine, Nicotinic Agonists and Donepezil, Cholinesterase Inhibitor, Enhance Performance of Memory tasks in Ovariecomized Rats," *Pharm. Biochem & Behav.*, 74:213-220 (2002).

Luther, et al., "A Muscle Acetylcholine Receptor is Expressed in the Human Cerebellar Medulloblastoma Cell Line TE671,"*J. Neurosci.* 9(3): 1082-1096 (1989).

Oswald, R.E., et al., "Characterization of nicotinic acetylcholine receptor channels of the TE671 human medulloblastoma clonal line," *Neurosci. Lett.* 96: 207-212 (1989).

Stratton, et al., "Characterization of the human cell line TE671," *Carcinogenesis* 10(5): 899-905 (1989).

Tracey, "The Inflammatory Reflex," *Nature* 420: 853-9 (2002).

Williams, et al., "Neuronal Nicotinic Acetylcholine Receptors," *Drug News Perspec.* 7(4): 205-223 (1994).

* cited by examiner

COMPOUNDS

CROSS REFERENCE TO RELATED APPLICATION

This application claims priority to PCT Application Number PCT/US2009/066083, with an International Filing Date of 30 Nov. 2009, which claims priority to, U.S. Provisional Patent Application Ser. No. 61/118,885, filed 1 Dec. 2008, each of which is herein incorporated by reference in its entirety.

FIELD OF THE INVENTION

The present invention relates to compounds that bind to and modulate the activity of neuronal nicotinic acetylcholine receptors, to novel salts thereof, to processes for preparing these compounds, to pharmaceutical compositions containing these compounds, and to methods of using these compounds for treating a wide variety of conditions and disorders, including those associated with dysfunction of the central nervous system (CNS).

BACKGROUND OF THE INVENTION

The therapeutic potential of compounds that target neuronal nicotinic receptors (NNRs), also known as nicotinic acetylcholine receptors (nAChRs), has been the subject of several reviews. See, for example, Breining et al., *Ann. Rep. Med. Chem.* 40: 3 (2005), Hogg and Bertrand, *Curr. Drug Targets: CNS Neurol. Disord.* 3: 123 (2004). Among the kinds of indications for which NNR ligands have been proposed as therapies are CNS disorders mentioned below. There exists a heterogeneous distribution of nAChR subtypes in both the central and peripheral nervous systems. For instance, the nAChR subtypes which are predominant in vertebrate brain are $\alpha 4\beta 2$, $\alpha 7$, and $\alpha 3\beta 2$, whereas those which predominate at the autonomic ganglia are $\alpha 3\beta 4$ and those of neuromuscular junction are $\alpha 1\beta 1\gamma\delta$ and $\alpha 1\beta 1\gamma\epsilon$.

A limitation of some nicotinic compounds is that they are associated with various undesirable side effects due to non-specific binding to multiple nAChR subtypes. For example, binding to and stimulation of muscle and ganglionic nAChR subtypes can lead to side effects which can limit the utility of a particular nicotinic binding compound as a therapeutic agent.

The commercial development of a drug candidate involves many steps, including the development of a cost effective synthetic method that is adaptable to a large scale manufacturing process. Commercial development also involves research regarding salt forms of the drug substance that exhibit suitable purity, chemical stability, pharmaceutical properties, and characteristics that facilitate convenient handling and processing. Furthermore, compositions containing the drug substance should have adequate shelf life. That is, they should not exhibit significant changes in physicochemical characteristics such as, but not limited to, chemical composition, water content, density, hygroscopicity, stability, and solubility upon storage over an appreciable period of time. Additionally, reproducible and constant plasma concentration profiles of drug upon administration to a patient are also important factors.

Solid salt forms are generally preferred for oral formulations due to their tendency to exhibit these properties in a preferential way; and in the case of basic drugs, acid addition salts are often preferred salt. However, different salt forms vary greatly in their ability to impart these properties and such properties cannot be predicted with reasonable accuracy. For example, some salts are solids at ambient temperatures, while other salts are liquids, viscous oils, or gums at ambient temperatures. Furthermore, some salt forms are stable to heat and light under extreme conditions and others readily decompose under much milder conditions. Salts also vary greatly in their hygroscopicity, the less hygroscopic being more advantageous. Thus, the development of a suitable acid addition salt form of a basic drug for use in a pharmaceutical composition is a highly unpredictable process.

Racemic 5-((E)-2-(pyrrolidin-3-yl)vinyl)-5-(tetrahydropyran-4-yloxy)pyridine, its synthesis, and its hemi-galactarate salt form are disclosed in WO 04/078752 which is incorporated by reference, and its counterparts. Because of the advantageous pharmacological properties of a single enantiomer over its racemate, there is a need for a stereospecific synthesis, preferably a process suitable for large-scale production. Furthermore, there is a need for salt forms that display improved properties, such as for example purity, stability, solubility, and bioavailability. Preferential characteristics of these novel salt forms include those that would increase the ease or efficiency of manufacture of the active ingredient and its pharmaceutical composition into a commercial drug product and improved stability of the drug over a prolonged period of time.

SUMMARY OF THE INVENTION

One aspect of the present invention is (R)-3-((E)-2-(pyrrolidin-3-yl)vinyl)-5-(tetrahydropyran-4-yloxy)pyridine mono-L-malate or a hydrate or solvate thereof. Another aspect is (R)-3-((E)-2-(pyrrolidin-3-yl)vinyl)-5-(tetrahydropyran-4-yloxy)pyridine hemi-galactarate or a hydrate or solvate thereof. Another aspect is (R)-3-((E)-2-(pyrrolidin-3-yl)vinyl)-5-(tetrahydropyran-4-yloxy)pyridine oxalate or a hydrate or solvate thereof. Another aspect is (R)-3-((E)-2-(pyrrolidin-3-yl)vinyl)-5-(tetrahydropyran-4-yloxy)pyridine di-p-toluoyl-D-tartrate or a hydrate or solvate thereof.

One aspect of the present invention is (R)-3-((E)-2-(pyrrolidin-3-yl)vinyl)-5-(tetrahydropyran-4-yloxy)pyridine or a pharmaceutically acceptable salt thereof substantially free of (S)-3-((E)-2-(pyrrolidin-3-yl)vinyl)-5-(tetrahydropyran-4-yloxy)pyridine. In one embodiment, (S)-3-((E)-2-(pyrrolidin-3-yl)vinyl)-5-(tetrahydropyran-4-yloxy)pyridine is present in an amount of less than 25% by weight. In one embodiment, (S)-3-((E)-2-(pyrrolidin-3-yl)vinyl)-5-(tetrahydropyran-4-yloxy)pyridine is present in an amount of less than 15% by weight. In one embodiment, (S)-3-((E)-2-(pyrrolidin-3-yl)vinyl)-5-(tetrahydropyran-4-yloxy)pyridine is present in an amount of less than 5% by weight. In one embodiment, (S)-3-((E)-2-(pyrrolidin-3-yl)vinyl)-5-(tetrahydropyran-4-yloxy)pyridine is present in an amount of less than 2% by weight. In one embodiment, (S)-3-((E)-2-(pyrrolidin-3-yl)vinyl)-5-(tetrahydropyran-4-yloxy)pyridine is present in an amount of less than 1% by weight. In one embodiment, the (R)-3-((E)-2-(pyrrolidin-3-yl)vinyl)-5-(tetrahydropyran-4-yloxy)pyridine is free of a significant amount of (S)-3-((E)-2-(pyrrolidin-3-yl)vinyl)-5-(tetrahydropyran-4-yloxy)pyridine.

One aspect of the present invention is a pharmaceutical composition comprising a compound as herein disclosed and one or more pharmaceutically acceptable adjuvant, carrier, or excipient. In one embodiment, the pharmaceutical composition further comprises one or more additional therapeutic agent.

One aspect of the present invention includes a compound (R)-3-((E)-2-(Pyrrolidin-3-yl)vinyl)-5-(tetrahydropyran-4-yloxy)pyridine mono-L-malate or hemi-galactarate or oxalate or di-p-toluoyl-D-tartrate for use as a medicament in treating a NNR mediated disorder.

Another aspect includes a method for the treatment or prevention of a NNR mediated disorder comprising administering to a mammal in need of such treatment, a therapeutically effective amount of (R)-3-((E)-2-(pyrrolidin-3-yl)vinyl)-5-(tetrahydropyran-4-yloxy)pyridine or a pharmaceutically acceptable salt thereof.

Another aspect includes use of a compound (R)-3-((E)-2-(pyrrolidin-3-yl)vinyl)-5-(tetrahydropyran-4-yloxy)pyridine or a pharmaceutically acceptable salt thereof in the preparation of a medicament for the treatment of a NNR mediated disorder.

In one embodiment of the aforementioned compound, method, or use, the disorder is selected from the group consisting of CNS disorders, inflammation, inflammatory response associated with bacterial and/or viral infection, pain, metabolic syndrome, autoimmune disorders. In one embodiment, the CNS disorder is selected from cognitive dysfunction in schizophrenia (CDS), Alzheimers Disease (AD), attention deficit disorder (ADD), pre-senile dementia (early onset of Alzheimer's Disease), dementia of the Alzheimer's type, mild cognitive impairment, age associated memory impairment and attention deficit hyperactivity disorder (ADHD).

Another aspect of the present invention includes an administration regimen of a pharmaceutical composition comprising administering (R)-3-((E)-2-(pyrrolidin-3-yl)vinyl)-5-(tetrahydropyran-4-yloxy)pyridine, or a pharmaceutically acceptable salt thereof in amounts of between 7 to 2200 µg/kg.

In the aspects and embodiments, another embodiment includes where the (R)-3-((E)-2-(pyrrolidin-3-yl)vinyl)-5-(tetrahydropyran-4-yloxy)pyridine is provided as the mono-L-malate, hemi-galactarate, oxalate, or di-p-toluoyl-D-tartrate salt thereof.

Another aspect includes novel intermediates, including diethyl(R)-2-(1-(tert-butoxycarbonyl)pyrrolidin-3-yl)malonate; (R)-2-(1-(tert-butoxycarbonyl)pyrrolidin-3-yl)malonic acid; tert-butyl(R)-3-(2-hydroxyethyl)pyrrolidine-1-carboxylate; and tert-butyl(R)-3-(2-iodoethyl)pyrrolidine-1-carboxylate.

Another aspect includes a method of making (R)-3-((E)-2-(pyrrolidin-3-yl)vinyl)-5-(tetrahydropyran-4-yloxy)pyridine through the intermediacy of one or more of diethyl(R)-2-(1-(tert-butoxycarbonyl)pyrrolidin-3-yl)malonate, (R)-2-(1-(tert-butoxycarbonyl)pyrrolidin-3-yl)malonic acid, tert-butyl (R)-3-(2-hydroxyethyl)pyrrolidine-1-carboxylate, and tert-butyl(R)-3-(2-iodoethyl)pyrrolidine-1-carboxylate.

Another aspect includes a method of making tert-butyl(R)-3-vinylpyrrolidine-1-carboxylate through the intermediacy of one or more of diethyl(R)-2-(1-(tert-butoxycarbonyl)pyrrolidin-3-yl)malonate, (R)-2-(1-(tert-butoxycarbonyl)pyrrolidin-3-yl)malonic acid, tert-butyl(R)-3-(2-hydroxyethyl) pyrrolidine-1-carboxylate, and tert-butyl(R)-3-(2-iodoethyl) pyrrolidine-1-carboxylate.

Another aspect includes a method of purifying (R)-3-((E)-2-(pyrrolidin-3-yl)vinyl)-5-(tetrahydropyran-4-yloxy)pyridine, with respect to isomeric (R)-3-((Z)-2-(pyrrolidin-3-yl) vinyl)-5-(tetrahydropyran-4-yloxy)pyridine and (R)-3-(1-(pyrrolidin-3-yl)vinyl)-5-(tetrahydropyran-4-yloxy) pyridine, by conversion to the oxalate salt and re-generation of the free base.

Combinations of aspects and embodiments form further embodiments of the present invention.

DETAILED DESCRIPTION

Definitions

The following definitions are meant to clarify, but not limit, the terms defined. If a particular term used herein is not specifically defined, such term should not be considered indefinite. Rather, terms are used within their accepted meanings.

As used herein, the term "compound(s)" may be used to mean the free base form, or alternatively, a salt form of (R)-3-((E)-2-(pyrrolidin-3-yl)vinyl)-5-(tetrahydropyran-4-yloxy)pyridine (Formula I), depending on the context, which will be readily apparent. Those skilled in the art will be able to distinguish the difference.

As used herein, the phrase "pharmaceutically acceptable" refers to carrier(s), diluent(s), excipient(s) or salt forms of the compound of Formula I that are compatible with the other ingredients of the composition and not deleterious to the recipient of the pharmaceutical composition.

As used herein, the phrase "pharmaceutical grade" refers to a compound or composition of a standard suitable for use as a medicine. With reference to the discussion herein, pharmaceutical grade compounds of the present invention, particularly salt forms thereof, display appropriate properties, including purity, stability, solubility, and bioavailability for use in a drug product. Preferential characteristics include those that would increase the ease or efficiency of manufacture of the active ingredient and its composition into a commercial drug product. Furthermore, pharmaceutical grade compounds of the present invention may be synthesized using a stereospecific synthesis that is scalable to a large-scale production, namely displaying adequate purity and yield.

As used herein, the term "pharmaceutical composition" refers to a compound of the present invention optionally admixed with one or more pharmaceutically acceptable carriers, diluents, or excipients. Pharmaceutical compositions preferably exhibit a degree of stability to environmental conditions so as to make them suitable for manufacturing and commercialization purposes.

As used herein, the terms "effective amount", "therapeutic amount", or "effective dose" refer to an amount of the compound of the present invention sufficient to elicit the desired pharmacological or therapeutic effects, thus resulting in effective prevention or treatment of a disorder. Prevention of the disorder may be manifested by delaying or preventing the progression of the disorder, as well as the onset of the symptoms associated with the disorder. Treatment of the disorder may be manifested by a decrease or elimination of symptoms, inhibition or reversal of the progression of the disorder, as well as any other contribution to the well being of the patient.

Figure 1:
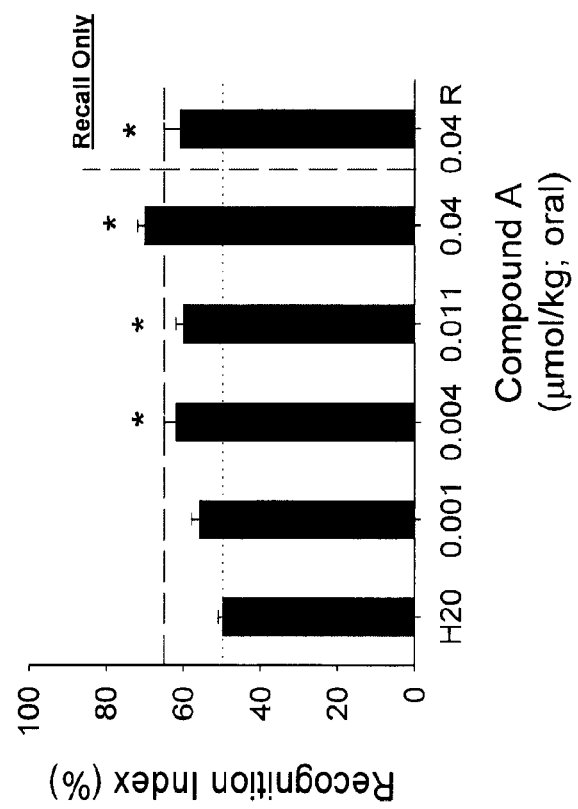
FIG. 1 depicts novel object recognition (NOR) vs. dose for (R)-3-((E)-2-(pyrrolidin-3-yl)vinyl)-5-(tetrahydropyran-4-yloxy)pyridine or a salt thereof, hereinafter referred to as Compound A. A statistically significant effect was observed for doses as low as 0.004 µM/kg.
Figure 1:
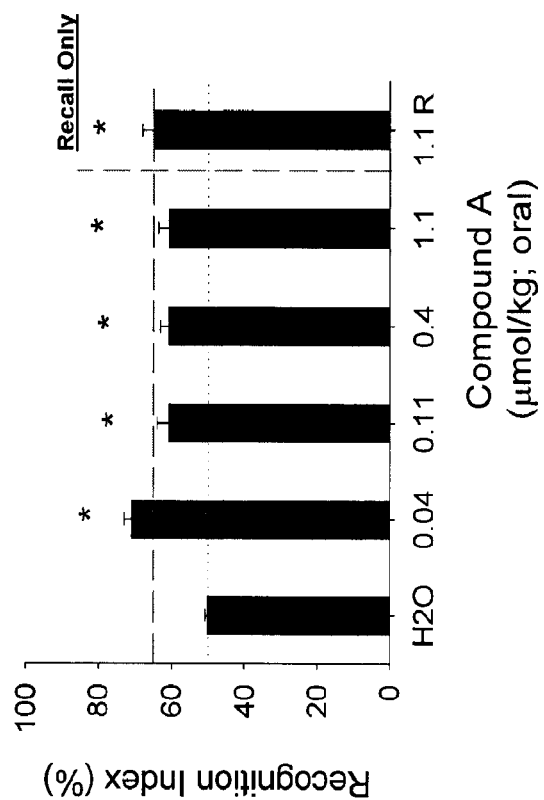
Figure 2:
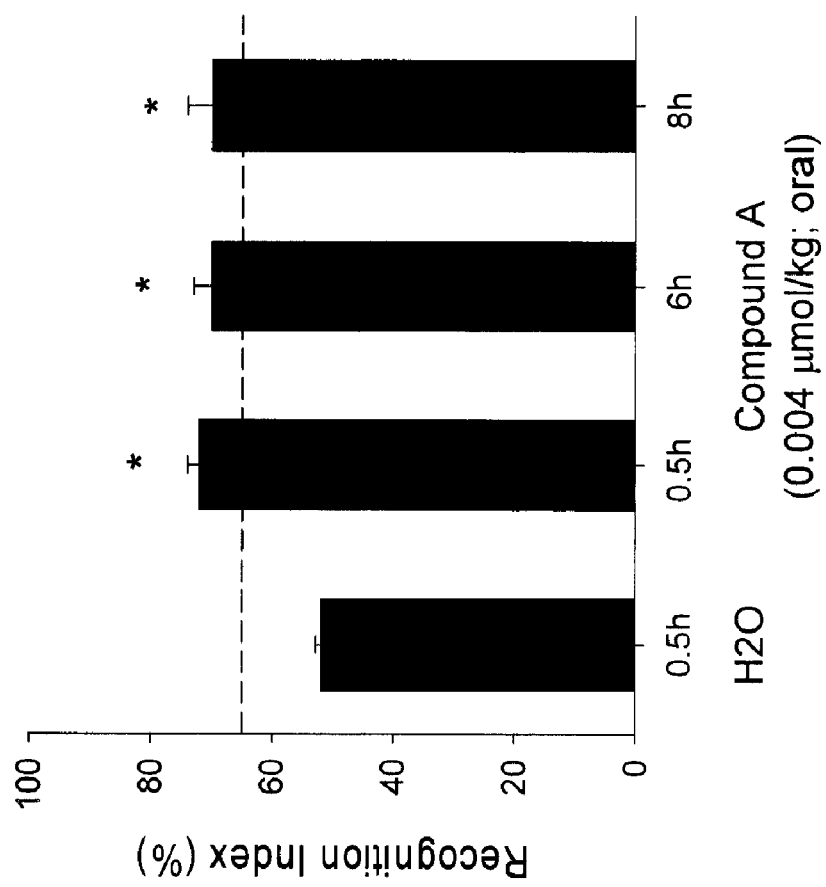
FIG. 2 depicts novel object recognition (NOR) vs. time for (R)-3-((E)-2-(pyrrolidin-3-yl)vinyl)-5-(tetrahydropyran-4-yloxy)pyridine or a salt thereof, Compound A, a dose at 0.004 µM/kg. A statistically significant effect was observed out to 8 h after dosing.

As will be discussed in more detail below and with reference to FIGS. 1 and 2, a statistically significant effect is observed for doses of the compound of Formula I, or a pharmaceutically acceptable salt thereof, as low as 0.004 µM/kg, including effects observed out to 8 h after dosing. The effective dose can vary, depending upon factors such as the condition of the patient, the severity of the symptoms of the disorder, and the manner in which the pharmaceutical composition is administered. Thus, as used herein, the effective dose may be less than 100 mg, in another embodiment less than 50 mg, in another embodiment less than 10 mg, or in another embodiment less than 1 mg. These effective doses typically represent the amount administered as a single dose, or as one or more doses administered over a 24 h period.

As used herein, the phrase "substantially' or 'sufficiently' quality, purity or pure, includes greater than 20%, preferably greater than 30%, and more preferably greater than 40% (e.g. greater than any of 50, 60, 70, 80, or 90%) quality or purity.

The term "stability" as defined herein includes chemical stability and solid state stability, where the phrase "chemical stability" includes the potential to store salts of the invention in an isolated form, or in the form of a pharmaceutical composition in which it is provided in admixture with pharmaceutically acceptable carriers, diluents, excipients, or adjuvants, such as in an oral dosage form, such as a tablet, capsule, or the like, under normal storage conditions, with an insignificant degree of chemical degradation or decomposition, and the phrase "solid state stability", includes the potential to store salts of the invention in an isolated solid form, or in the form of a solid pharmaceutical composition in which it is provided in admixture with pharmaceutically acceptable carriers, diluents, excipients, or adjuvants, such as in an oral dosage form, such as a tablet, capsule, or the like, under normal storage conditions, with an insignificant degree of solid state transformation, such as crystallization, recrystallization, solid state phase transition, hydration, dehydration, solvation, or desolvation.

Examples of "normal storage conditions" include one or more of temperatures of between −80° C. and 50° C., preferably between 0° C. and 40° C. and more preferably ambient temperatures, such as 15° C. to 30° C., pressures of between 0.1 and 2 bars, preferably at atmospheric pressure, relative humidity of between 5 and 95%, preferably 10 to 60%, and exposure to 460 lux or less of UV/visible light, for prolonged periods, such as greater than or equal to six months. Under such conditions, salts of the invention may be found to be less than 5%, more preferably less than 2%, and especially less than 1%, chemically degraded or decomposed, or solid state transformed, as appropriate. The skilled person will appreciate that the above-mentioned upper and lower limits for temperature, pressure, and relative humidity represent extremes of normal storage conditions, and that certain combinations of these extremes will not be experienced during normal storage (e.g. a temperature of 50° C. and a pressure of 0.1 bar).

As used herein, the term "disorder", unless stated otherwise, means any condition, dysfunction, or disease associated with NNR receptor activity.

Compounds

One embodiment of the present invention relates to (R)-3-((E)-2-(pyrrolidin-3-yl)vinyl)-5-(tetrahydropyran-4-yloxy) pyridine (Formula I) or a pharmaceutically acceptable salt thereof.

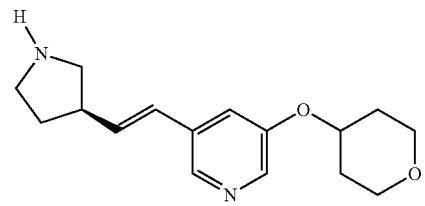

Formula I

As will be appreciated by those skilled in the art, different naming conventions may name a compound differently. Thus, Compound A may be named (R)-3-((E)-2-(pyrrolidin-3-yl) vinyl)-5-(tetrahydropyran-4-yloxy)pyridine or, alternatively, (R)-3-(2-pyrrolidin-3-yl)-vinyl)-5-((tetrahydro-2H-pyran-4-yl)oxy)pyridine. Such naming conventions should not be used to introduce ambiguity to this specification.

In one embodiment, the compound of Formula I or a pharmaceutically acceptable salt thereof is substantially pure. In one embodiment, the compound of Formula I or a pharmaceutically acceptable salt thereof is substantially free of (S)-3-((E)-2-(pyrrolidin-3-yl)vinyl)-5-(tetrahydropyran-4-yloxy)pyridine. In one embodiment, the compound of Formula I or a pharmaceutically acceptable salt thereof is present in an amount of about 75% by weight compared to (S)-3-((E)-2-(pyrrolidin-3-yl)vinyl)-5-(tetrahydropyran-4-yloxy)pyridine, preferably greater than 85% by weight, more preferably greater than 95% by weight, more preferably greater than 98% by weight, and most preferably 99% by weight or greater. One embodiment relates to 100% pure (R)-3-((E)-2-(pyrrolidin-3-yl)vinyl)-5-(tetrahydropyran-4-yloxy)pyridine (Formula I).

Process

One embodiment of the present invention relates to a method for the preparation of (R)-3-((E)-2-(pyrrolidin-3-yl) vinyl)-5-(tetrahydropyran-4-yloxy)pyridine or a pharmaceutically acceptable salt thereof substantially free of (S)-3-((E)-2-(pyrrolidin-3-yl)vinyl)-5-(tetrahydropyran-4-yloxy) pyridine by weight. Another embodiment of the present invention relates to a method for the preparation of (R)-3-((E)-2-(pyrrolidin-3-yl)vinyl)-5-(tetrahydropyran-4-yloxy) pyridine or a pharmaceutically acceptable salt thereof containing less than 25%, preferably less than 15%, more preferable less than 5%, even more preferably less than 2%, and most preferably less than 1% of (S)-3-((E)-2-(pyrrolidin-3-yl)vinyl)-5-(tetrahydropyran-4-yloxy)pyridine by weight, without the use of a chiral chromatographic separation step. In one embodiment of the present invention, a method for the manufacture of substantially pure (R)-3-((E)-2-(pyrrolidin-3-yl)vinyl)-5-(tetrahydropyran-4-yloxy)pyridine is provided, without reliance upon chromatographic separation.

General Synthetic Methods

Racemic 3-((E)-2-(pyrrolidin-3-yl)vinyl)-5-(tetrahydropyran-4-yloxy)pyridine can be synthesized as reported in PCT WO2004/078752, herein incorporated by reference, using a palladium catalyzed coupling of tert-butyl 3-vinylpyrrolidine-1-carboxylate with the 3-bromo-5-(tetrahydro-2H-pyran-4-yloxy)pyridine, followed by removal of the tert-butoxycarbonyl protecting group. In the racemic synthesis, the requisite tert-butyl 3-vinylpyrrolidine-1-carboxylate was produced by treating tert-butyl 3-formylpyrrolidine-1-carboxylate with methylenetriphenylphosphorane (Wittig reagent). While tert-butyl 3-formylpyrrolidine-1-carboxylate can be made by several methods, it was not an ideal intermediate for a single enantiomer synthesis, in that it is susceptible to racemization during the Wittig reaction. Thus, a new synthetic route, one characterized by stereochemical fidelity, was devised.

The compounds may be prepared according to the following methods using commercially available starting materials and reagents.

(R)-3-((E)-2-(Pyrrolidin-3-yl)vinyl)-5-(tetrahydropyran-4-yloxy)pyridine may be prepared via palladium catalyzed coupling of tert-butyl(R)-3-vinylpyrrolidine-1-carboxylate (compound 9) and 3-bromo-5-(tetrahydro-2H-pyran-4-yloxy)-pyridine (compound 12) as outlined in Scheme 3.

The preparation of compound 9 is outlined in Scheme 1. Commercially available tert-butyl(R)-3-hydroxypyrrolidine-1-carboxylate (compound 1) is treated with methanesulfonyl chloride to give tert-butyl(R)-3-(methylsulfonyloxy)pyrrolidine-1-carboxylate (compound 2), which then is reacted with diethylmalonate and a suitable base (e.g., potassium tert-butoxide or sodium ethoxide) to give diethyl (R)-2-(1-(tert-butoxycarbonyl)pyrrolidin-3-yl)malonate (compound 3) with inverted stereochemistry around the chiral carbon. Suitable solvents for these reactions may be selected from the group of toluene, xylenes,1-methyl-2-pyrrolidinone, dimethylformamide, dimethylacetamide, ethanol, tert-butanol, tetrahydrofuran, 1,2-dimethoxyethane, dioxane, and mixtures thereof. In one embodiment the solvent for the methanesulfonic ester formation toluene, and the solvent for the malonate displacement is 1-methyl-2-pyrrolidinone. In another embodiment the solvent for the malonate displacement is ethanol. Suitable bases for these reactions may be selected from the group of triethylamine, diethylisopropylamine, diisopropylethylamine, potassium tert-butoxide, sodium metal, sodium hydride, sodium ethoxide, potassium hydride and lithium hydride. In one embodiment the base for the methanesulfonic ester formation is triethylamine, and the base for the malonate displacement is potassium tert-butoxide. In another embodiment the base for the malonate displacement is sodium ethoxide.

Hydrolysis of diester 3 with aqueous potassium hydroxide yields (R)-2-(1-(tert-butoxycarbonyl)pyrrolidin-3-yl)malonic acid (compound 4), which is decarboxylated to afford (R)-2-(1-(tert-butoxycarbonyl)pyrrolidin-3-yl)acetic acid (compound 5). Suitable solvents for these reactions may be selected from the group of water, ethanol, tetrahydrofuran, dimethylformamide, dimethylacetamide, 1,2-dimethoxyethane, dioxane, 1-methyl-2-pyrrolidinone, toluene, dimethylsulfoxide, and mixtures thereof. In one embodiment the solvent for the ester hydrolysis is aqueous tetrahydrofuran, and the solvent for the decarboxylation is 1-methyl-2-pyrrolidinone. In another embodiment the solvent for the ester hydrolysis is ethanol, and the solvent for the decarboxylation is a mixture of dimethylsufloxide and toluene. Suitable bases for the hydrolysis reaction may be selected from the group of potassium hydroxide, sodium hydroxide, potassium carbonate, sodium carbonate, barium hydroxide and cesium carbonate. In one embodiment the base is potassium hydroxide.

Reduction of compound 5 gives tert-butyl(R)-3-(2-hydroxyethyl)pyrrolidine-1-carboxylate (compound 6), which may be reacted with methanesulfonyl chloride and then sodium iodide to give tert-butyl(R)-3-(2-(methylsulfonyloxy)ethyl)pyrrolidine-1-carboxylate (compound 7) and tert-butyl(R)-3-(2-iodoethyl)pyrrolidine-1-carboxylate (compound 8), respectively. Suitable solvents for the reduction reaction may be selected from the group of tetrahydrofuran, ether, dioxane, 1,2-dimethoxyethane, and mixtures thereof. In one embodiment the solvent is tetrahydrofuran. Suitable reducing agents may be selected from the group of borane, diborane, borane-tetrahydrofuran complex, borane-dimethyl ether complex and borane-dimethylsulfide complex. Suitable solvents for the methanesulfonic ester formation may be selected from the group of toluene, xylenes, ether, tetrahydrofuran, 1,2-dimethoxyethane, dioxane, and mixtures thereof. In one embodiment the solvent for the methanesulfonic ester formation is toluene. Suitable bases for the methanesulfonic ester formation may be selected from the group of triethylamine, diethylisopropylamine and diisopropylethylamine. In one embodiment the base for the methanesulfonic ester formation is triethylamine. Suitable solvents for the iodide displacement may be selected from the group of 1-methyl-2-pyrrolidinone, dimethylformamide, dimethylacetamide, ethanol, tertbutanol, tetrahydrofuran, 1,2-dimethoxyethane, dioxane, dimethylsulfoxide, and mixtures thereof. In one embodiment the solvent for the iodide displacement is 1,2-dimethoxyethane.

Finally, treatment of compound 8 with potassium tert-butoxide gives of compound 9. Suitable solvents for this reaction may be selected from the group of 1,2-dimethoxyethane, 1-methyl-2-pyrrolidinone, dimethylformamide, dimethylacetamide, ethanol, tetrahydrofuran, dioxane and mixtures thereof. In one embodiment the solvent is 1,2-dimethoxyethane. Suitable bases for this reaction may be selected from the group of potassium tert-butoxide, sodium ethoxide and diazabicycloundecane. In another embodiment the base is potassium tert-butoxide.

One embodiment of the invention relates to a process for the preparation of compound 9 using the reaction steps as outlined in Scheme 1 and in the discussion above.

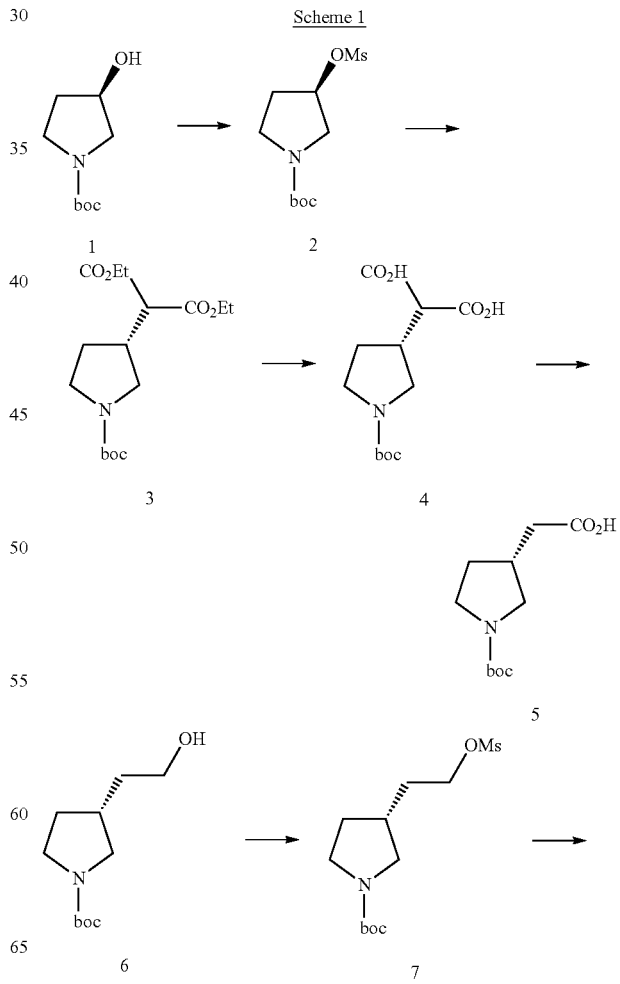

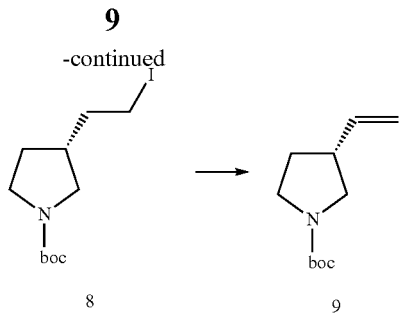

The preparation of 3-bromo-5-(tetrahydro-2H-pyran-4-yloxy)-pyridine (compound 12) is outlined in Scheme 2. Coupling of 3-bromo-5-hydroxypyridine (compound 10) with 4-hydroxytetrahydro-2H-pyran (compound 11) gives compound 12. Suitable conditions for the coupling include those in which a phosphine (e.g., triphenylphosphine) and an azo compound (e.g., diethyl azodicarboxylate, also known as DEAD) are used, in an inert solvent, to effect the coupling (e.g., toluene). Alternately, other conditions, in which the oxo anion of 3-bromo-5-hydroxypyridine displaces a leaving group from the 4-position of tetrahydropyran, may be employed.

One embodiment of the invention relates to a process for the preparation of compound 12 using the reaction steps as outlined in Scheme 2 and above.

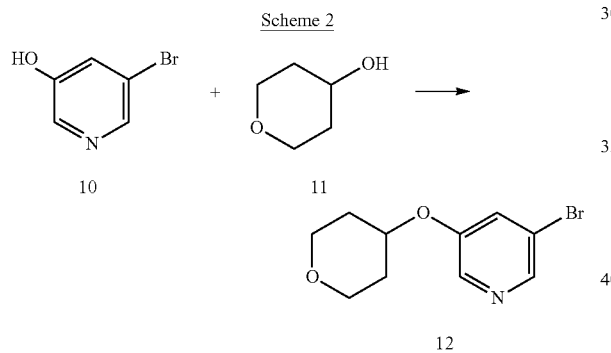

The final steps in the preparation of (R)-3-((E)-2-(pyrrolidin-3-yl)vinyl)-5-(tetrahydropyran-4-yloxy)pyridine (free base form) is illustrated in Scheme 3. Compounds 9 and 12 are coupled via a palladium acetate mediated coupling reaction to afford tert-butyl(R)-(E)-3-(2-(5-(tetrahydro-2H-pyran-4-yloxy)pyridin-3-yl)vinyl)pyrrolidine-1-carboxylate (also known as (R)-5-(1-(tert-butoxycarbonyl)-(E)-2-(pyrrolidin-3-yl)vinyl)-5-(tetrahydropyran-4-yloxy)pyridine, compound 13), which is de-protected to give (R)-3-((E)-2-(pyrrolidin-3-yl)vinyl)-5-(tetrahydropyran-4-yloxy)pyridine (compound 14). Suitable solvents for the palladium-catalyzed coupling reaction may be selected from the group of 1-methyl-2-pyrrolidinone, dimethylformamide, dimethylacetamide and acetonitrile. In one embodiment the solvent is 1-methyl-2-pyrrolidinone. Suitable bases for the palladium catalyzed coupling reaction may be selected from the group of triethylamine, diethylisopropylamine, diisopropylethylamine. In one embodiment the base is diisopropylethylamine. Suitable phosphine ligands for the palladium catalyzed coupling reaction may be selected from the group of tri-n-butylphosphine, tri-tert-butylphosphine, tricyclohexylphosphine, triphenylphosphine and tri-o-tolylphosphine. In one embodiment the phosphine ligand is tricyclohexylphosphine. Suitable palladium catalysts for the palladium catalyzed coupling reaction may be selected from the group of palladium acetate, palladium chloride and dipalladium tris (dibenzylacetone). In one embodiment the palladium catalyst is palladium acetate. Suitable solvents for the de-protection reaction may be selected from the group of water, dichloromethane, chloroform and dichloroethane. In one embodiment the solvent is dichloromethane. In another embodiment the solvent for the de-protection reaction is water.

Suitable acids for the de-protection reaction may be selected from the group of trifluoroacetic acid, hydrochloric acid and sulfuric acid. In one embodiment the acid is trifluoroacetic acid.

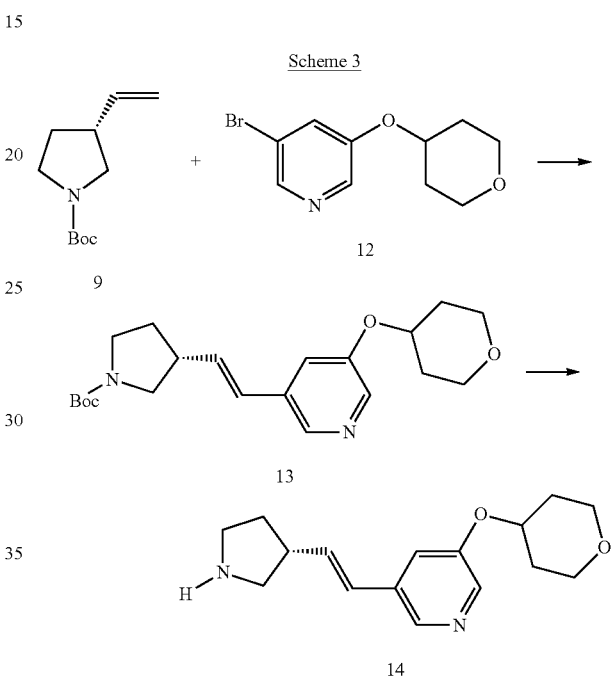

One embodiment of the invention relates to a process for the preparation of compound 14 using the reaction steps as outlined above in Schemes 1, 2 and 3. The invention further relates to a process for the preparation of the salt form of (R)-3-((E)-2-(pyrrolidin-3-yl)vinyl)-5-(tetrahydropyran-4-yloxy)pyridine malate comprising the additional step of reacting the free base with L-malic acid in a mixture of 2-propanol and isopropyl acetate or other suitable solvent as described below.

Another embodiment of the invention relates to the formation of the oxalate salt of compound 14 and the use of the oxalate salt as a purification intermediate in the production of compound 14. The palladium catalyzed coupling of compounds 9 and 12 produces a mixture of materials in which compound 13 predominates, typically representing 75-80% of the coupling products. The remaining coupling products include the corresponding Z isomer, tert-butyl(R)-(Z)-3-(2-(5-(tetrahydro-2H-pyran-4-yloxy)pyridin-3-yl)vinyl)pyrrolidine-1-carboxylate, and a so-called "exo" isomer, tert-butyl (R)-3-(1-(5-(tetrahydro-2H-pyran-4-yloxy)pyridin-3-yl) vinyl)pyrrolidine-1-carboxylate, typically representing ~5% and up to 20% of the coupling products respectively. Removal of these minor isomers from the major, desired isomer was unexpectedly and conveniently accomplished by de-protection of the mixture of isomers, followed by conversion of the free base to the oxalate salt. Initial precipitation of the oxalate salt in water/2-propanol mixtures, for example, gives compound 14 in which the isomeric impurities are reduced to <1% each or better. Further purification can be accomplished by recrystallization.

Examples of compounds of the present invention which are labeled with a radioisotope appropriate to various diagnostic uses are for example, $^{11}$C- or $^{18}$F-labeled analogs of compound 14 which would be suitable for use in positron emission tomography.

Unless otherwise stated, structures depicted herein are also meant to include compounds which differ only in the presence of one or more isotopically enriched atoms. For example, compounds having the present structure except for the replacement of a hydrogen atom by deuterium or tritium, or the replacement of a carbon atom by $^{13}$C or $^{14}$C, or the replacement of a nitrogen atom by $^{15}$N, or the replacement of an oxygen atom with $^{17}$O or $^{18}$O are within the scope of the invention. Such isotopically labeled compounds are useful as research or diagnostic tools.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts, *Protecting Groups in Organic Synthesis*, 3$^{rd}$ Edition, John Wiley & Sons, New York (1999)). These groups are removed at a convenient stage of the compound synthesis using methods that are readily apparent to those skilled in the art. The selection of processes as well as the reaction conditions and order of their execution shall be consistent with the preparation of compounds of the present invention.

The present invention also provides a method for the synthesis of novel compounds useful as intermediates, such as diethyl(R)-2-(1-(tert-butoxycarbonyl)pyrrolidin-3-yl)malonate (compound 3), (R)-2-(1-(tert-butoxycarbonyl)pyrrolidin-3-yl)malonic acid (compound 4), tert-butyl(R)-3-(2-hydroxyethyl)pyrrolidine-1-carboxylate (compound 6), and tert-butyl(R)-3-(2-iodoethyl)pyrrolidine-1-carboxylate (compound 8).

Salt Forms

One aspect of the present invention relates to novel salt forms of (R)-3-((E)-2-(pyrrolidin-3-yl)vinyl)-5-(tetrahydropyran-4-yloxy)pyridine. (R)-3-((E)-2-(pyrrolidin-3-yl)vinyl)-5-(tetrahydropyran-4-yloxy)pyridine in the free base form is a viscous oil with limited water solubility. However, the free base may react with both inorganic and organic acids to make acid addition salts that have physical properties that are advantageous for the preparation of pharmaceutical compositions such as crystallinity, water solubility, and stability toward chemical degradation.

The present invention relates to pharmaceutically acceptable salts of (R)-3-((E)-2-(pyrrolidin-3-yl)vinyl)-5-(tetrahydropyran-4-yloxy)pyridine. Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or solvates, such as ethanol solvates.

One embodiment of the present invention relates to acid addition salts of (R)-3-((E)-2-(pyrrolidin-3-yl)vinyl)-5-(tetrahydropyran-4-yloxy)pyridine wherein the acid is selected from hydrochloric acid, methane sulphonic acid, maleic acid, phosphoric acid, 1-hydroxy-2-naphthoic acid, malonic acid, L-tartaric acid, fumaric acid, citric acid, L-malic acid, R-mandelic acid, S-mandelic acid, succinic acid, 4-acetamidobenzoic acid, adipic acid, galactaric acid, di-p-toluoyl-D-tartaric acid, oxalic acid, D-glucuronic acid, 4-hydroxybenzoic acid, 4-methoxybenzoic acid, (1S)-(+)-10-camphorsulfonic acid, (1R,3S)-(+)-camphoric acid, and p-toluenesulfonic acid. The present invention also includes hydrates and solvates of these salt forms.

The stoichiometry of the salts comprised in the present invention may vary. For example, it is typical that the molar ratio of acid to (R)-3-((E)-2-(pyrrolidin-3-yl)vinyl)-5-(tetrahydropyran-4-yloxy)pyridine is 1:2 or 1:1, but other ratios, such as 3:1, 1:3, 2:3, 3:2 and 2:1, may be possible and are likewise included in the scope of the present invention.

Depending upon the manner by which the salts described herein are formed, the salts may have crystalline structures that occlude solvents that are present during salt formation. Thus, the salts may occur as hydrates and other solvates of varying stoichiometry of solvent relative to (R)-3-((E)-2-(pyrrolidin-3-yl)vinyl)-5-(tetrahydropyran-4-yloxy)pyridine.

In one embodiment of the present invention, the salt has a stoichiometry of acid to (R)-3-((E)-2-(pyrrolidin-3-yl)vinyl)-5-(tetrahydropyran-4-yloxy)pyridine of 1:2. In another embodiment, the salt has a stoichiometry of acid to (R)-3-((E)-2-(pyrrolidin-3-yl)vinyl)-5-(tetrahydropyran-4-yloxy)pyridine of 1:1.

Another embodiment of the present invention relates to (R)-3-((E)-2-(pyrrolidin-3-yl)vinyl)-5-(tetrahydropyran-4-yloxy)pyridine mono-L-malate or a hydrate or solvate thereof.

Another embodiment of the present invention relates to (R)-3-((E)-2-(pyrrolidin-3-yl)vinyl)-5-(tetrahydropyran-4-yloxy)pyridine hemi-galactarate or a hydrate or solvate thereof.

Another embodiment of the present invention relates to (R)-3-((E)-2-(pyrrolidin-3-yl)vinyl)-5-(tetrahydropyran-4-yloxy)pyridine oxalate or a hydrate or solvate thereof.

Another embodiment of the present invention relates to (R)-3-((E)-2-(pyrrolidin-3-yl)vinyl)-5-(tetrahydropyran-4-yloxy)pyridine di-p-toluoyl-D-tartrate or a hydrate or solvate thereof.

One embodiment of the present invention relates to the following salts of (R)-3-((E)-2-(pyrrolidin-3-yl)vinyl)-5-(tetrahydropyran-4-yloxy)pyridine;

4-Acetamidobenzoic
Adipic
(1 R,3S)-(+)-Camphoric
(1 S)-(+)-1 O-Camphorsulfonic
Citric
Fumaric
D-glucuronic
Hydrochloric
4-Hydroxybenzoic
1-Hydroxy-2-naphthoic (Xinafoic)
Maleic
L-Malic
Malonic
(R)-Mandelic
(S)-Mandelic
Methanesulfonic

| |
|---|
| 4-Methoxybenzoic |
| Phosphoric |
| Succinic |
| L-Tartaric |
| p-Toluenesulfonic•H20 | or a hydrate or solvate thereof.

A further aspect of the present invention relates to processes for the preparation of the salts. The salts may be obtained by crystallization under controlled conditions.

The invention also relates to a process for the preparation (R)-3-((E)-2-(pyrrolidin-3-yl)vinyl)-5-(tetrahydropyran-4-yloxy)pyridine salt forms comprising the following steps:
(i) mixing the free base, or a solution of the free base of substantially pure (R)-3-((E)-2-(pyrrolidin-3-yl)vinyl)-5-(tetrahydropyran-4-yloxy)pyridine in a suitable solvent, with any of the acids mentioned above in pure form or as a solution of any of the acids in a suitable solvent, typically 0.5 to 1 equivalents of the acid;
(ii)(a) cooling the resulting salt solution if necessary to cause precipitation, or
(ii)(b) adding a suitable anti-solvent to cause precipitation, or
(ii)(c) evaporating the solvent and adding and new solvent and repeating either steps (ii)(a) or step (ii)(b); and
(iii) filtering and collecting the salt.

The stoichiometry, solvent mix, solute concentration, and temperature employed may vary.

Representative solvents that may be used to prepare or recrystallize the salt forms include, without limitation, ethanol, methanol, propanol, 2-propanol, isopropyl acetate, acetone, ethyl acetate, toluene, water, methyl ethyl ketone, methyl isobutyl ketone, tert-butyl methyl ether, tetrahydrofuran, dichloromethane, n-heptane, and acetonitrile.

In one embodiment the solvent is selected from ethanol, propanol, isopropyl acetate, water, hexane, or mixtures thereof, and the temperature used for precipitation is between 16° C. and 25° C.

In one embodiment the acid is L-malic acid, and the solvent used is 2-propoanol alone or in combination with isopropyl acetate. In another embodiment the acid is oxalic acid, and the solvent used is aqueous 2-propanol.

In a further embodiment, the salts are (R)-3-((E)-2-(pyrrolidin-3-yl)vinyl)-5-(tetrahydropyran-4-yloxy)pyridine mono-L-malate or hemi-galactarate or oxalate or di-p-toluoyl-D-tartrate.

The stability of the obtained salts may be demonstrated in a variety of ways. Propensity to gain and release atmospheric moisture may be assessed by dynamic vapor sorption (DVS).

Methods of Treatment (R)-3-((E)-2-(pyrrolidin-3-yl)vinyl)-5-(tetrahydropyran-4-yloxy)pyridine, or pharmaceutically acceptable salts thereof, or a pharmaceutical composition comprising said compounds may be used for the prevention or treatment of various conditions or disorders for which other types of nicotinic compounds have been proposed or are shown to be useful as therapeutics, such as CNS disorders, inflammation, inflammatory response associated with bacterial and/or viral infection, pain, metabolic syndrome, autoimmune disorders or other disorders described in further detail herein. The compounds may also be used as a diagnostic agent in receptor binding studies (in vitro and in vivo). Such therapeutic and other teachings are described, for example, in references previously listed herein, including Williams et al., *Drug News Perspec.* 7(4): 205 (1994), Arneric et al., *CNS Drug Rev.* 1(1): 1-26 (1995), Arneric et al., *Exp. Opin. Invest. Drugs* 5(1): 79-100 (1996), Bencherif et al., *J. Pharmacol. Exp. Ther.* 279: 1413 (1996), Lippiello et al., *J. Pharmacol. Exp. Ther.* 279: 1422 (1996), Damaj et al., *J. Pharmacol. Exp. Ther.* 291: 390 (1999); Chiari et al., *Anesthesiology* 91: 1447 (1999), Lavand'homme and Eisenbach, *Anesthesiology* 91: 1455 (1999), Holladay et al., *J. Med. Chem.* 40(28): 4169-94 (1997), Bannon et al., *Science* 279: 77 (1998), PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al.

One embodiment of the present invention relates to use of (R)-3-((E)-2-(pyrrolidin-3-yl)vinyl)-5-(tetrahydropyran-4-yloxy)pyridine or a pharmaceutically acceptable salt thereof in the manufacture of a medicament.

Another embodiment of the present invention relates to use of (R)-3-((E)-2-(pyrrolidin-3-yl)vinyl)-5-(tetrahydropyran-4-yloxy)pyridine mono-L-malate or hemi-galactarate or oxalate or di-p-toluoyl-D-tartrate for use as a medicament.

One embodiment of the present invention relates to a method for the treatment or prevention of central nervous system (CNS) disorders, comprising administering to a mammal in need of such treatment, a therapeutically effective amount of (R)-3-((E)-2-(pyrrolidin-3-yl)vinyl)-5-(tetrahydropyran-4-yloxy)pyridine or a pharmaceutically acceptable salt thereof or the mono-L-malate or hemi-galactarate or oxalate or di-p-toluoyl-D-tartrate. More specifically, the disorder may be selected from the group consisting of CNS disorders, inflammation, inflammatory response associated with bacterial and/or viral infection, pain, metabolic syndrome, autoimmune disorders or other disorders described in further detail herein.

One embodiment of the present invention relates to a pharmaceutical composition comprising a therapeutically effective amount of (R)-3-((E)-2-(pyrrolidin-3-yl)vinyl)-5-(tetrahydropyran-4-yloxy)pyridine or a pharmaceutically acceptable salt thereof or the mono-L-malate or hemi-galactarate or oxalate or di-p-toluoyl-D-tartrate salt thereof and one or more pharmaceutically acceptable carrier, diluents, excipients, or adjuvant.

One embodiment of the present invention relates to the use of a pharmaceutical composition of the present invention in the manufacture of a medicament for treatment of CNS disorders.

Another embodiment of the present invention relates to use of (R)-3-((E)-2-(pyrrolidin-3-yl)vinyl)-5-(tetrahydropyran-4-yloxy)pyridine or a pharmaceutically acceptable salt thereof, or the mono-L-malate or hemi-galactarate or oxalate or di-p-toluoyl-D-tartrate salt thereof, in the manufacture of a medicament for treatment or prevention of disorders mediated by NNR.

Another embodiment of the present invention relates to a method of modulating NNR in a subject in need thereof through the administration of (R)-3-((E)-2-(pyrrolidin-3-yl) vinyl)-5-(tetrahydropyran-4-yloxy)pyridine or a pharmaceutically acceptable salt thereof or the mono-L-malate or hemi-galactarate or oxalate or di-p-toluoyl-D-tartrate salt thereof.

CNS Disorders ((R)-3-((E)-2-(pyrrolidin-3-yl)vinyl)-5-(tetrahydropyran-4-yloxy)pyridine, or a pharmaceutically acceptable salt thereof, or the mono-L-malate or hemi-galactarate or oxalate or di-p-toluoyl-D-tartrate salt thereof, or a pharmaceutical composition comprising said compounds are useful in the treatment or prevention of a variety of CNS disorders, including neurodegenerative disorders, neuropsychiatric disorders, neurologic disorders, and addictions. The compounds and their pharmaceutical compositions may be used to treat or prevent cognitive deficits and dysfunctions, age-related and otherwise; attentional disorders and dementias, including those due to infectious agents or metabolic disturbances; to provide neuroprotection; to treat convulsions and multiple cerebral infarcts; to treat mood disorders, compulsions and addictive behaviors; to provide analgesia; to control inflammation, such as mediated by cytokines and nuclear factor kappa B; to treat inflammatory disorders; to provide pain relief; and to treat infections, as anti-infectious agents for treating bacterial, fungal, and viral infections. Among the disorders, diseases and conditions that the compounds and pharmaceutical compositions of the present invention may be used to treat or prevent are: age-associated memory impairment (AAMI), mild cognitive impairment (MCI), age-related cognitive decline (ARCD), pre-senile dementia, early onset Alzheimer's disease, senile dementia, dementia of the Alzheimer's type, Alzheimer's disease, cognitive impairment no dementia (CIND), Lewy body dementia, HIV-dementia, AIDS dementia complex, vascular dementia, Down syndrome, head trauma, traumatic brain injury (TBI), dementia pugilistica, Creutzfeld-Jacob Disease and prion diseases, stroke, ischemia, attention deficit disorder, attention deficit hyperactivity disorder, dyslexia, schizophrenia, schizophreniform disorder, schizoaffective disorder, cognitive dysfunction in schizophrenia, cognitive deficits in schizophrenia, Parkinsonism including Parkinson's disease, postencephalitic parkinsonism, parkinsonism-dementia of Gaum, frontotemporal dementia Parkinson's Type (FTDP), Pick's disease, Niemann-Pick's Disease, Huntington's Disease, Huntington's chorea, tardive dyskinesia, hyperkinesia, progressive supranuclear palsy, progressive supranuclear paresis, restless leg syndrome, Creutzfeld-Jakob disease, multiple sclerosis, amyotrophic lateral sclerosis (ALS), motor neuron diseases (MND), multiple system atrophy (MSA), corticobasal degeneration, Guillain-Barré Syndrome (GBS), and chronic inflammatory demyelinating polyneuropathy (CIDP), epilepsy, autosomal dominant nocturnal frontal lobe epilepsy, mania, anxiety, depression, premenstrual dysphoria, panic disorders, bulimia, anorexia, narcolepsy, excessive daytime sleepiness, bipolar disorders, generalized anxiety disorder, obsessive compulsive disorder, rage outbursts, oppositional defiant disorder, Tourette's syndrome, autism, drug and alcohol addiction, tobacco addiction, and eating disorders.

Cognitive impairments or dysfunctions may be associated with psychiatric disorders or conditions, such as schizophrenia and other psychotic disorders, including but not limited to psychotic disorder, schizophreniform disorder, schizoaffective disorder, delusional disorder, brief psychotic disorder, shared psychotic disorder, and psychotic disorders due to a general medical conditions, dementias and other cognitive disorders, including but not limited to mild cognitive impairment, pre-senile dementia, Alzheimer's disease, senile dementia, dementia of the Alzheimer's type, age-related memory impairment, Lewy body dementia, vascular dementia, AIDS dementia complex, dyslexia, Parkinsonism including Parkinson's disease, cognitive impairment and dementia of Parkinson's Disease, cognitive impairment of multiple sclerosis, cognitive impairment caused by traumatic brain injury, dementias due to other general medical conditions, anxiety disorders, including but not limited to panic disorder without agoraphobia, panic disorder with agoraphobia, agoraphobia without history of panic disorder, specific phobia, social phobia, obsessive-compulsive disorder, post-traumatic stress disorder, acute stress disorder, generalized anxiety disorder and generalized anxiety disorder due to a general medical condition, mood disorders, including but not limited to major depressive disorder, dysthymic disorder, bipolar depression, bipolar mania, bipolar I disorder, depression associated with manic, depressive or mixed episodes, bipolar II disorder, cyclothymic disorder, and mood disorders due to general medical conditions, sleep disorders, including but not limited to dyssomnia disorders, primary insomnia, primary hypersomnia, narcolepsy, parasomnia disorders, nightmare disorder, sleep terror disorder and sleepwalking disorder, mental retardation, learning disorders, motor skills disorders, communication disorders, pervasive developmental disorders, attention-deficit and disruptive behavior disorders, attention deficit disorder, attention deficit hyperactivity disorder, feeding and eating disorders of infancy, childhood, or adults, tic disorders, elimination disorders, substance-related disorders, including but not limited to substance dependence, substance abuse, substance intoxication, substance withdrawal, alcohol-related disorders, amphetamine or amphetamine-like-related disorders, caffeine-related disorders, cannabis-related disorders, cocaine-related disorders, hallucinogen-related disorders, inhalant-related disorders, nicotine-related disorders, opioid-related disorders, phencyclidine or phencyclidine-like-related disorders, and sedative-, hypnotic- or anxiolytic-related disorders, personality disorders, including but not limited to obsessive-compulsive personality disorder and impulse-control disorders.

The above conditions and disorders are discussed in further detail, for example, in the American Psychiatric Association: Diagnostic and Statistical Manual of Mental Disorders, Fourth Edition, Text Revision, Washington, D.C., American Psychiatric Association, 2000. This Manual may also be referred to for greater detail on the symptoms and diagnostic features associated with substance use, abuse, and dependence.

One embodiment relates to a method of treating or preventing CNS disorders in a subject in need thereof comprising administering to said subject ((R)-3-((E)-2-(pyrrolidin-3-yl)vinyl)-5-(tetrahydropyran-4-yloxy)pyridine, or a pharmaceutically acceptable salt thereof, or the mono-L-malate or hemi-galactarate or oxalate or di-p-toluoyl-D-tartrate salt thereof, or a pharmaceutical composition comprising said compounds.

In another embodiment the CNS disorders are selected from cognitive dysfunction in schizophrenia (CDS), Alzheimers Disease (AD), attention deficit disorder (ADD), pre-senile dementia (early onset of Alzheimer's Disease), dementia of the Alzheimer's type, mild cognitive impairment, age associated memory impairment and attention deficit hyperactivity disorder (ADHD). In one embodiment the CNS disorders are selected from memory improvement and learning improvement.

Inflammation

The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, "The inflammatory reflex," *Nature* 420: 853-9 (2002)). Excessive inflammation and tumor necrosis factor synthesis cause morbidity and even mortality in a variety of diseases. These diseases include, but are not limited to, endotoxemia, rheumatoid arthritis, osteoarthritis, psoriasis, asthma, atherosclerosis, idiopathic pulmonary fibrosis, and inflammatory bowel disease.

Inflammatory conditions that may be treated or prevented by administering the compounds described herein include, but are not limited to, chronic and acute inflammation, psoriasis, endotoxemia, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, acute cholangitis, aphteous stomatitis, pouchitis, glomerulonephritis, lupus nephritis, thrombosis, and graft vs. host reaction.

Inflammatory Response Associated with Bacterial and/or Viral Infection

Many bacterial and/or viral infections are associated with side effects brought on by the formation of toxins, and the body's natural response to the bacteria or virus and/or the toxins. As discussed above, the body's response to infection often involves generating a significant amount of TNF and/or other cytokines. The over-expression of these cytokines can result in significant injury, such as septic shock (when the bacteria is sepsis), endotoxic shock, urosepsis, viral pneumonitis, and toxic shock syndrome.

Cytokine expression is mediated by NNRs, and may be inhibited by administering agonists or partial agonists of these receptors. Those compounds described herein that are agonists or partial agonists of these receptors may therefore be used to minimize the inflammatory response associated with bacterial infection, as well as viral and fungal infections. Examples of such bacterial infections include anthrax, botulism, and sepsis. Some of these compounds may also have antimicrobial properties.

The compounds of the present invention may also be used as adjunct therapy in combination with existing therapies to manage bacterial, viral and fungal infections, such as antibiotics, antivirals and antifungals. Antitoxins may also be used to bind to toxins produced by the infectious agents and allow the bound toxins to pass through the body without generating an inflammatory response. Examples of antitoxins are disclosed, for example, in U.S. Pat. No. 6,310,043 to Bundle et al. Other agents effective against bacterial and other toxins may be effective and their therapeutic effect may be complemented by co-administration with the compounds described herein.

Pain

The compounds may be administered to treat and/or prevent pain, including acute, neurologic, inflammatory, neuropathic and chronic pain. The analgesic activity of compounds described herein may be demonstrated in models of persistent inflammatory pain and of neuropathic pain, performed as described in U.S. Published Patent Application No. 20010056084 A1 (Allgeier et al.) (e.g., mechanical hyperalgesia in the complete Freund's adjuvant rat model of inflammatory pain and mechanical hyperalgesia in the mouse partial sciatic nerve ligation model of neuropathic pain).

The analgesic effect is suitable for treating pain of various genesis or etiology, in particular in treating inflammatory pain and associated hyperalgesia, neuropathic pain and associated hyperalgesia, chronic pain (e.g., severe chronic pain, post-operative pain and pain associated with various conditions including cancer, angina, renal or biliary colic, menstruation, migraine and gout). Inflammatory pain may be of diverse genesis, including arthritis and rheumatoid disease, tenosynovitis and vasculitis. Neuropathic pain includes trigeminal or herpetic neuralgia, neuropathies, diabetic neuropathy pain, causalgia, low back pain and deafferentation syndromes such as brachial plexus avulsion.

One embodiment relates to a method of treating pain in a subject in need thereof comprising administering to said subject ((R)-3-((E)-2-(pyrrolidin-3-yl)vinyl)-5-(tetrahydropyran-4-yloxy)pyridine, or a pharmaceutically acceptable salt thereof, or the mono-L-malate or hemi-galactarate or oxalate or di-p-toluoyl-D-tartrate salt thereof, or a pharmaceutical composition comprising said compounds.

Other Disorders

In addition to treating CNS disorders, inflammation, and pain, the compounds of the present invention may be also used to prevent or treat certain other conditions, diseases, and disorders in which NNRs play a role. Examples include autoimmune disorders such as lupus, disorders associated with cytokine release, cachexia secondary to infection (e.g., as occurs in AIDS, AIDS related complex and neoplasia), obesity, pemphitis, urinary incontinence, retinal diseases, infectious diseases, myasthenia, Eaton-Lambert syndrome, dystonia, hypertension, osteoporosis, vasoconstriction, vasodilatation, cardiac arrhythmias, type I diabetes, type II diabetes, ulcers, bulimia, anorexia, constipation, and diarrhea, as well as those indications set forth in published PCT application WO 98/25619. The compounds of this invention may also be administered to treat convulsions such as those that are symptomatic of epilepsy, and to treat conditions such as syphillis and Creutzfeld-Jakob disease.

Diagnostic Uses

Another embodiment of the present invention relates to compounds that have utility as diagnostic agents and in receptor binding studies as described herein.

The compounds may be used in diagnostic compositions, such as probes, particularly when they are modified to include appropriate labels. The probes may be used, for example, to determine the relative number and/or function of specific receptors, particularly the α4β2 receptor subtype. For this purpose the compounds of the present invention most preferably are labeled with a radioactive isotopic moiety such as $^{11}C$, $^{18}F$, $^{76}Br$, $^{123}I$ or $^{125}I$.

One embodiment of the invention relates to ((R)-3-((E)-2-(pyrrolidin-3-yl)vinyl)-5-(tetrahydropyran-4-yloxy)pyridine, or a pharmaceutically acceptable salt thereof, or the mono-L-malate or hemi-galactarate or oxalate or di-p-toluoyl-D-tartrate salt thereof, wherein one to three of the atoms represents a detectable isotope selected from $^3H$, $^{19}F$ and $^{13}C$, or wherein one of the atoms is a detectable isotope selected from $^{18}F$, $^{11}C$ and $^{14}C$.

The administered compounds may be detected using known detection methods appropriate for the label used. Examples of detection methods are scintillation counting, position emission topography (PET), single-photon emission computed tomography (SPECT), gamma imaging, magnetic resonance imaging (MRI) or magnetic resonance spectroscopy (MRS). The radiolabels described above are useful in PET (e.g., $^{11}C$, $^{18}F$ or $^{76}Br$) and SPECT (e.g., $^{123}I$) imaging, with half-lives of about 20.4 min for $^{11}C$, about 109 min for $^{18}F$, about 13 h for $^{123}I$, and about 16 h for $^{76}Br$. A high specific activity is desired to visualize the selected receptor subtypes at non-saturating concentrations. The administered doses typically are low and provide high contrast images. Determination of dose is carried out in a manner known to one skilled in the art of radiolabel imaging. The compounds may be administered in compositions that incorporate other ingredients, such as those types of ingredients that are useful in formulating a diagnostic composition. Compounds useful in accordance with carrying out the present invention most preferably are employed in forms of high purity. After the compounds are administered to a subject (e.g., a human subject), the presence of that compound within the subject may be imaged and quantified by appropriate techniques in order to indicate the presence, quantity, and functionality of selected NNR subtypes. In addition to humans, the compounds may also be administered to animals, such as mice, rats, horses, dogs, and monkeys. SPECT and PET imaging may be carried out using any appropriate technique and apparatus. The radiolabeled compounds bind with high affinity to selective NNR subtypes (e.g., α4β2) and preferably exhibit negligible non-specific binding to other nicotinic cholinergic receptor subtypes (e.g., those receptor subtypes associated with muscle and ganglia). As such, the compounds may be used as agents for noninvasive imaging of nicotinic cholinergic receptor subtypes within the body of a subject, particularly within the brain for diagnosis associated with a variety of CNS diseases and disorders.

In one aspect, the diagnostic compositions may be used in a method to diagnose disease in a subject, such as a human patient. The method involves administering to that patient a detectably labeled compound as described herein, and detecting the binding of that compound to selected NNR subtypes (e.g., α4β2 receptor subtypes). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, such as Alzheimer's disease, Parkinson's disease, and schizophrenia or any disorder herein mentioned.

Receptor Binding

The compounds of this invention may be used as reference ligands in binding assays for compounds which bind to NNR subtypes, particularly the α4β2 receptor subtypes. For this purpose the compounds of this invention are preferably labeled with a radioactive isotopic moiety such as $^3$H, or $^{14}$C. Examples of such binding assays are described in detail below.

Pharmaceutical Compositions

In one aspect the present invention relates to pharmaceutical compositions comprising the compound of the present invention and one or more pharmaceutically acceptable carrier, diluent, or excipient. Another aspect of the invention provides a process for the preparation of a pharmaceutical composition including admixing the compound of the present invention with one or more pharmaceutically acceptable carrier, diluent, or excipient.

The manner in which the compound of the present invention is administered may vary. The compound of the present invention is preferably administered orally. Preferred pharmaceutical compositions for oral administration include tablets, capsules, caplets, syrups, solutions, and suspensions. The pharmaceutical compositions of the present invention may be provided in modified release dosage forms such as time-release tablet and capsule formulations.

The pharmaceutical compositions may also be administered via injection, namely, intravenously, intramuscularly, subcutaneously, intraperitoneally, intraarterially, intrathecally, and intracerebroventricularly. Carriers for injection may include 5% dextrose solutions, saline, and phosphate buffered saline.

The compositions may also be administered using other means, for example, rectal administration. The compounds may also be administered by inhalation, for example, in the form of an aerosol; topically, such as, in lotion form; transdermally, such as, using a transdermal patch (for example, by using technology that is commercially available from Novartis and Alza Corporation), by powder injection, or by buccal, sublingual, or intranasal absorption.

Pharmaceutical compositions may be formulated in unit dose form, or in multiple or subunit doses forms.

The administration of the pharmaceutical compositions described herein may be intermittent, or at a gradual, continuous, constant or controlled rate. The pharmaceutical compositions may be administered to a warm-blooded animal, for example, a mammal such as a mouse, rat, cat, guinea pig, rabbit, horses, dog, pig, cow, or monkey; but advantageously is administered to a human being.

Combinations

The compound of the present invention may be used in the treatment of a variety of disorders and conditions and, as such, may be used in combination with a variety of other therapeutic agents useful in the treatment or prophylaxis of those disorders. Thus, one embodiment of the present invention relates to the administration of the compound of the present invention in combination with other therapeutic agents. For example, the compound of the present invention may be used in combination with other NNR ligands (such as varenicline), antioxidants (such as free radical scavenging agents), antibacterial agents (such as penicillin antibiotics), antiviral agents (such as nucleoside analogs, like zidovudine and acyclovir), anticoagulants (such as warfarin), anti-inflammatory agents (such as NSAIDs), anti-pyretics, analgesics, anesthetics (such as used in surgery), acetylcholinesterase inhibitors (such as donepezil and galantamine), antipsychotics (such as haloperidol, clozapine, olanzapine, and quetiapine), immuno-suppressants (such as cyclosporin and methotrexate), neuroprotective agents, steroids (such as steroid hormones), corticosteroids (such as dexamethasone, predisone, and hydrocortisone), vitamins, minerals, nutraceuticals, anti-depressants (such as imipramine, fluoxetine, paroxetine, escitalopram, sertraline, venlafaxine, and duloxetine), anxiolytics (such as alprazolam and buspirone), anticonvulsants (such as phenytoin and gabapentin), vasodilators (such as prazosin and sildenafil), mood stabilizers (such as vaiproate and aripiprazole), anti-cancer drugs (such as antiproliferatives), antihypertensive agents (such as atenolol, clonidine, amlopidine, verapamil, and olmesartan), laxatives, stool softeners, diuretics (such as furosemide), anti-spasmotics (such as dicyclomine), anti-dyskinetic agents, and anti-ulcer medications (such as esomeprazole). Such a combination of therapeutic agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the present invention with other therapeutic agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second. Such sequential administration may be close in time or remote in time.

Another aspect of the present invention relates to combination therapy comprising administering to the subject a therapeutically or prophylactically effective amount of the compound of the present invention and one or more other therapeutic agents including chemotherapeutics, radiation therapuetic agents, gene therapeutic agents, or agents used in immunotherapy.

Low Dose ((R)-3-((E)-2-(Pyrrolidin-3-yl)vinyl)-5-(tetrahydropyran-4-yloxy)pyridine or a salt thereof is a substrate for Pgp brain pump which is located in the blood brain barrier. The Pgp pump is responsible for pumping substances out of the brain.

Due to this pump, it is often difficult to get drugs into the brain in therapeutically effective amounts. This often results in the administration of high doses of drugs, which at these high levels may have side effects in other parts of the human body. ((R)-3-((E)-2-(Pyrrolidin-3-yl)vinyl)-5-(tetrahydropyran-4-yloxy)pyridine, although being a substrate for the PGP pump, can be administered at low doses while at the same time have a relatively long duration of effect. For example, compared to acetylcholine, the natural agonist for NNR, the response for ((R)-3-((E)-2-(pyrrolidin-3-yl)vinyl)-5-(tetrahydropyran-4-yloxy)pyridine is twice as great in the in vitro assay at $\alpha 4\beta 2$.

One embodiment of the invention relates to administration of a pharmaceutical composition comprising ((R)-3-((E)-2-(pyrrolidin-3-yl)vinyl)-5-(tetrahydropyran-4-yloxy)pyridine, or a pharmaceutically acceptable salt thereof, in certain embodiments, the mono-L-malate or hemi-galactarate or oxalate or di-p-toluoyl-D-tartrate salt thereof, in amounts of between 1 to 2200 µg/day. In another embodiment the amount is 50 to 1500 µg/day. In a further embodiment the amount is 50 to 1000 µg/day. In one embodiment the amount is 50 to 500 µg/day. In another embodiment the amount is 75 to 300 µg/day. In yet another embodiment the amount is 75 to 200 µg/day. In yet a further embodiment the amount is 75 to 150 µg/day.

The dose of ((R)-3-((E)-2-(pyrrolidin-3-yl)vinyl)-5-(tetrahydropyran-4-yloxy)pyridine, or a pharmaceutically acceptable salt thereof, oin certain embodiments, the mono-L-malate or hemi-galactarate or oxalate or di-p-toluoyl-D-tartrate salt thereof, may be administered one, two, or three times daily. One embodiment relates to once daily administration. Another embodiment relates to twice daily administration.

Another embodiment of the invention relates to a NNR agonist which has a half life ($t_{1/2}$) between 5 and 8 hours. In one embodiment the $t_{1/2}$ is between 6 and 7 hours. In another embodiment the $t_{1/2}$ is 6.8 hours.

Another embodiment of the invention relates to a NNR agonist which has a duration of action between 5 and 10 hours. In one embodiment the duration is between 6 to 9 hours. In a further embodiment the duration is 8 hours.

In a further embodiment the agonist is an $\alpha 4\beta 2$ agonist.

In yet another embodiment the agonist is ((R)-3-((E)-2-(pyrrolidin-3-yl)vinyl)-5-(tetrahydropyran-4-yloxy)pyridine.

EXAMPLES

The following examples are provided to illustrate the present invention, and should not be construed as limiting thereof. In these examples, all parts and percentages are by weight, unless otherwise noted.

Example 1

Instrumentation and Experimental Protocols for Characterization of (R)-3-((E)-2-(pyrrolidin-3-yl) vinyl)-5-(tetrahydropyran-4-yloxy)pyridine and its Salt Forms Nuclear Magnetic Resonance (NMR) Spectrometry NMR spectra were collected on either a Varian Unity 300 MHz instrument or a Bruker 400 MHz instrument equipped with an auto-sampler and controlled by a DRX400 console. Automated experiments were acquired using ICONNMR v4.0.4 (build 1) running with Topspin v 1.3 (patch level 8) using the standard Bruker loaded experiments. For non-routine spectroscopy, data were acquired through the use of Topspin alone.

Melting Point

A Fisher-Johns hot stage melting point apparatus was used, at a setting corresponding to a heating rate of about 5° C. per min.

Differential Scanning Calorimetry (DSC)

DSC data were collected on a TA Instruments Q1000 or a Mettler DSC 823e equipped with a 50 position auto-sampler. The instrument was calibrated for energy and temperature calibration using certified indium. Typically 0.5-1.5 mg of each sample, in a pin-holed aluminium pan, was heated at 10° C./min from 25° C. to 175-200° C. A nitrogen purge at 30 mL/min was maintained over the sample.

Dynamic Vapor Sorption (DVS)

Sorption isotherms were determined using a SMS DVS Intrinsic moisture sorption analyzer controlled by SMS Analysis suite software. The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically a 5-20 mg sample was placed on the tared mesh stainless steel basket under ambient conditions. The sample was loaded and unloaded at 40% RH and 25° C. (typical ambient conditions). A moisture sorption isotherm was performed as outlined below (2 scans giving 1 complete cycle). The standard isotherm was performed at 25° C. at 10% RH intervals over a 0-90% RH range.

DVS Generic Method Parameters

| Parameters | Values |
|---|---|
| Adsorption - Scan 1 | 40-90 |
| Desorption/Adsorption - Scan 2 | 90-Dry, Dry-40 |
| Intervals (% RH) | 10 |
| Number of Scans | 2 |
| Flow rate (mL/min) | 200 |
| Temperature (° C.) | 25 |
| Stability (° C./min) | 0.2 |
| Sorption Time (h) | 6 hour time out |

Chemical Purity by HPLC

Purity analysis was performed on an Agilent HP1100 series system equipped with a diode array detector and using ChemStation software vB.02.01-SR1.

HPLC Method Parameters for Chemical Purity Determination:

| | |
|---|---|
| Sample Preparation | 0.5 mg/mL in acetonitrile:water 1:1 (v/v) |
| Column: | Phenomenex Luna C18 (2), 150 × 4.6 mm, 5 µm |
| Column Temperature (° C.): | 25 |
| Injection (µL): | 5 |
| Detection: Wavelength, Bandwidth(nm): | 255, 90 |
| Flow Rate (mL/min): | 1 |
| Phase A: | 0.1% TFA in water |
| Phase B: | 0.085% TFA in acetonitrile |

-continued

Timetable:

| Time (min) | % Phase A | % Phase B |
|---|---|---|
| 0 | 95 | 5 |
| 25 | 5 | 95 |
| 25.2 | 95 | 5 |
| 30 | 95 | 5 |

Ion Chromatography

Data were collected on a Metrohm 761 Advanced Compact IC (for cations) and a Metrohm 861 Advanced Compact IC (for anions) using IC Net software v2.3. Samples were prepared as 1000 ppm stocks in DMSO. Samples were diluted to 100 ppm with DMSO prior to testing. Quantification was achieved by comparison with standard solutions of known concentration of the ion being analyzed.

Ion Chromatography Method for Anions:

| Type of method | Anion exchange |
|---|---|
| Column: | Metrosep A Supp 5 - 250 (4.0 × 250 mm) |
| Column Temperature (° C.): | Ambient |
| Injection (μL): | 20 |
| Detection: | Conductivity detector |
| Flow Rate (mL/min): | 0.7 |
| Eluent: | 3.2 mM sodium carbonate, 1.0 mM sodium hydrogen carbonate in water |

Ion Chromatography Method for Cations:

| Type of method | Cation exchange |
|---|---|
| Column: | Metrosep C 2 - 250 (4.0 × 250 mm) |
| Column Temperature (° C.): | Ambient |
| Injection (μL): | 20 |
| Detection: | Conductivity detector |
| Flow Rate (mL/min): | 1.0 |
| Eluent: | 4.0 mM Tartaric acid, 0.75 mM Dipicolinic acid in water |

Example 2

Synthesis of tert-butyl(R)-3-(methylsulfonyloxy)pyrrolidine-1-carboxylate (2)

Procedure A: To a solution of tert-butyl(R)-3-hydroxypyrrolidine-1-carboxylate (200 g, 1.07 mol) and triethylamine (167 g, 1.63 mol) in toluene (700 mL) at −20 to −30° C. was added methanesulfonyl chloride (156 g, 1.36 mol) drop-wise while maintaining the temperature at −10 to −20° C. The solution was warmed to ambient temperature and allowed to stir. The reaction solution was sampled hourly and analyzed by HPLC to establish completion of the reaction. Upon completion of the reaction, the suspension was filtered to remove the triethylamine hydrochloride. The filtrate was washed with ~600 mL of dilute aqueous sodium bicarbonate solution. The organic layer was dried and concentrated under reduced pressure to give 2 as a viscous oil (260 g, 92%) which is used without further purification. $^1$H NMR (CDCl$_3$, 400 MHz) δ5.27 (m, 1H), 3.44-3.76 (m, 4H), 3.05 (s, 3H), 2.26 (m, 1H), 2.15 (m, 1H), 1.47 (s, 9H).

Procedure B: A reactor was charged with tert-butyl(R)-3-hydroxypyrrolidine-1-carboxylate (2.00 kg, 10.7 mol), toluene (8.70 kg) and triethylamine (1.75 kg, 17.3 mol). The reactor was flushed with nitrogen for 15 min. The mixture was stirred and cooled to 3° C. Methanesulfonyl chloride (1.72 kg, mol) was slowly added (over a 2 h period) with continuous ice bath cooling (exothermic reaction) (after complete addition, the temperature was 14° C.). The mixture, now viscous with precipitated triethylamine hydrochloride, was stirred 12 h as it warmed to 20° C. Both GC and TLC analysis (ninhydrin stain) indicated that no starting material remained. The mixture was filtered to remove the triethylamine hydrochloride, and the filtrate was returned to the reactor. The filtrate was then washed (2×3 kg) with 5% aqueous sodium bicarbonate, using 15 min of stirring and 15 min of settling time for each wash. The resulting organic layer was dried over anhydrous sodium sulfate and filtered. The volatiles were removed from the filtrate under vacuum, first at 50° C. for 4 h and then at ambient temperature for 10 h. The residue weighed 3.00 kg (106% yield) and was identical by chromatographic and NMR analysis to previously prepared samples, with the exception that it contained toluene.

Example 3

Synthesis of diethyl(R)-2-(1-(tert-butoxycarbonyl)pyrrolidin-3-yl)malonate (3)

Preparation A: To a solution of potassium tert-butoxide (187 g, 1.62 mol) in 1-methyl-2-pyrrolidinone (1.19 L) was added diethyl malonate (268 g. 1.67 mol) while maintaining the temperature below 35° C. The solution was heated to 40° C. and stirred for 20-30 min. tert-Butyl(R)-3-(methylsulfonyloxyl)pyrrolidine-1-carboxylate (112 g, 420 mmol) was added and the solution was heated to 65° C. and stirred for 6 h. The reaction solution was sampled every 2 h and analyzed by HPLC to establish completion of the reaction. Upon completion of reaction (10-12 h), the mixture was cooled to around 25° C. De-ionized water (250 mL) was added to the solution, and the pH was adjusted to 3-4 by addition of 2N hydrochloric acid (650 mL). The resulting suspension was filtered, and water (1.2 L) and chloroform (1.4 L) were added. The solution was mixed thoroughly, and the chloroform layer was collected and evaporated under reduced pressure to give a yellow oil. The oil was dissolved in hexanes (2.00 L) and washed with deionized water (2×1.00 L). The organic layer was concentrated under reduced pressure at 50-55° C. to give a pale yellow oil (252 g) which $^1$H NMR analysis indicates to be 49.1% of 3 (123.8 g) along with 48.5% diethyl malonate (122 g), and 2% of 1-methyl-2-pyrrolidinone (5 g). The material was carried forward into the next step without further purification. $^1$H NMR (CDCl$_3$, 400 MHz) δ 4.20 (q, 4H), 3.63 (m, 1H), 3.48 (m, 1H), 3.30 (m, 1H), 3.27 (d, J=10 Hz, 1H), 3.03 (m, 1H), 2.80 (m, 1H), 2.08 (m, 1H), 1.61 (m, 1H), 1.45 (s, 9H), 1.27 (t, 6H).

Preparation B: A reactor, maintained under a nitrogen atmosphere, was charged with 200 proof ethanol (5.50 kg) and 21% (by weight) sodium ethoxide in ethanol (7.00 kg, 21.6 mol). The mixture was stirred and warmed to 30° C. Diethyl malonate (3.50 kg, 21.9 mol) was added over a 20 min period. The reaction mixture was then warmed at 40° C. for 1.5 h. A solution of tert-butyl(R)-3-(methylsulfonyloxyl)pyrrolidine-1-carboxylate (3.00 kg of the product from Example 2, Procedure B, 10.7 mol) in 200 proof ethanol (5.50 kg) was added, and the resulting mixture was heated at reflux (78° C.) for 2 h. Both GC and TLC analysis (ninhydrin stain) indicated that no starting material remained. The stirred mixture was then cooled to 25° C., diluted with water (2.25 kg), and treated slowly with a solution of concentrated hydrochloric acid (1.27 kg, 12.9 mol) in water (5.44 kg). This mixture was washed twice with methyl tert-butyl ether (MTBE) (14.1 kg and 11.4 kg), using 15 min of stirring and 15 min of settling time for each wash. The combined MTBE washes were dried over anhydrous sodium sulfate (1 kg), filtered and concentrated under vacuum at 50° C. for 6 h. The residue (red oil) weighed 4.45 kg and was 49% desired product by GC analysis (62% overall yield from tert-butyl(R)-3-hydroxypyrrolidine-1-carboxylate).

Example 4

Synthesis of (R)-2-(1-(tert-butoxycarbonyl)pyrrolidin-3-yl)malonic acid (4)

Procedure A: To a solution of the product of Example 3, Procedure A (232 g), containing 123.8 g (380 mmol) of 3 and 121.8 g (760 mmol) of diethyl malonate, in tetrahydrofuran (1.2 L) was added a 21% potassium hydroxide solution (450 g in 0.50 L of deionized water) while maintaining the temperature below 25° C. The reaction mixture was heated to 45° C. and stirred for 1 h. The reaction solution was sampled every hour and analyzed by HPLC to establish completion of the reaction. Upon completion of reaction (2-3 h), the mixture was cooled to around 25° C. The aqueous layer was collected and cooled to 5° C. The pH was adjusted to 2 by addition of 4N hydrochloric acid (750 mL), and the resulting suspension was held at 5-10° C. for 30 min. The mixture was filtered, and the filter cake was washed with hexanes (1 L). The aqueous filtrate was extracted with chloroform (1 L) and the chloroform layer was put aside. The solids collected in the filtration step were re-dissolved in chloroform (1 L) by heating to 40° C. The solution was filtered to remove un-dissolved inorganic solids. The chloroform layers were combined and concentrated under reduced pressure at 50-55° C. to give an off-white solid (15 g). The solids were combined and dissolved in ethyl acetate (350 mL) to give a suspension that was warmed to 55-60° C. for 2 h. The suspension was filtered while hot and the resulting cake washed with ethyl acetate (2×150 mL) and hexanes (2×250 mL) to give 83.0 g (80.1%) of 4 as a white solid which was used in the next step without further purification. $^1$H NMR (d$_4$-CH$_3$OH, 400 MHz) δ 3.60 (m, 1H), 3.46 (m, 1H), 3.29-3.32 (m, 2H), 2.72 (m, 1H), 2.09 (m, 1H), 1.70 (m, 1H), 1.45 (s, 9H).

Procedure B: A solution of the product of Example 3, Procedure B (4.35 kg), containing 2.13 kg (6.47 mol) of 3, in tetrahydrofuran (13.9 kg) was added to a stirred, cooled solution of potassium hydroxide (1.60 kg, 40.0 mol) in deionized water (2.00 kg) under a nitrogen atmosphere, while maintaining the temperature below 35° C. The reaction mixture was heated and maintained at 40-45° C. for 24 h, by which time GC and TLC analysis indicated that the reaction was complete. The mixture was cooled to 25° C. and washed with MTBE (34 kg), using 15 min of stirring and 15 min of settling time. The aqueous layer was collected and cooled to 1° C. A mixture of concentrated hydrochloric acid (2.61 kg, 26.5 mol) in deionized water (2.18 kg) was then added slowly, keeping the temperature of the mixture at <15° C. during and for 15 min after the addition. The pH of the solution was adjusted to 3.7 by further addition of hydrochloric acid. The white solid was collected by filtration, washed with water (16 kg), and vacuum dried at ambient temperature for 6 d. The dry solid weighed 1.04 kg. The filtrate was cooled to <10° C. and kept at that temperature as the pH was lowered by addition of more hydrochloric acid (1.6 L of 6 N was used; 9.6 mol; final pH=2). The white solid was collected by filtration, washed with water (8 L), and vacuum dried at 40° C. for 3 d. The dry solid weighed 0.25 kg. The combined solids (1.29 kg, 73% yield) were chromatographically identical to previously prepared samples.

Example 5

Synthesis of (R)-2-(1-(tert-butoxycarbonyl)pyrrolidin-3-yl)acetic acid (5)

Procedure A: A solution of (R)-2-(1-(tert-butoxycarbonyl) pyrrolidin-3-yl)malonic acid (83 g) in 1-methyl-2-pyrrolidinone (0.42 L) was stirred under nitrogen at 110-112° C. for 2 h. The reaction solution was sampled every hour and analyzed by HPLC to establish completion of the reaction. Upon completion of reaction the reaction solution was cooled to 20-25° C. The solution was mixed with de-ionized water (1.00 L), and MTBE (1.00 L) was added. The phases were separated, and the organic layer was collected. The aqueous phase was extracted with MTBE (1.00 L), then chloroform (1.00 L). The organic layers were combined and concentrated under reduced pressure at 50-55° C. to give an oil. This oil was dissolved in MTBE (2.00 L) and washed twice with 0.6N hydrochloric acid (2×1.00 L). The organic layer was collected and concentrated under reduced pressure at 50-55° C. to give a semi-solid. The semi-solid was suspended in 1:4 ethyl acetate/hexanes (100 mL), heated to 50° C., held for 30 min, cooled to −10° C., and filtered. The filtrate was concentrated under reduced pressure to give an oil, which was dissolved in MTBE (250 mL) and washed twice with 0.6N hydrochloric acid (2×100 mL). The organic layer was concentrated under reduced pressure at 50-55° C. to give a semi-solid which was suspended in 1:4 ethyl acetate/hexanes (50 mL), heated to 50° C., held for 30 min, cooled to −10° C., and filtered. The solids were collected, suspended in hexanes (200 mL), and collected by filtration to give 54.0 g (77.6%) of 5. $^1$H NMR (CDCl$_3$, 400 MHz) δ 11.00 (br s, 1H), 3.63 (m, 1H), 3.45 (M, 1H), 3.30 (M, 1H), 2.97 (m, 1H), 2.58 (m, 1H), 2.44 (m, 2H), 2.09 (m, 1H), 1.59 (M, 1H), 1.46 (s, 9H).

Procedure B: A solution of (R)-2-(1-(tert-butoxycarbonyl) pyrrolidin-3-yl)malonic acid (1.04 kg, 3.81 mol) in 1-methyl-2-pyrrolidinone (6.49 kg) was stirred under nitrogen at 110° C. for 5 h, by which time TLC and HPLC analysis indicated that the reaction was complete. The reaction mixture was cooled to 25° C. (4 h) and combined with water (12.8 kg) and MTBE (9.44 kg). The mixture was stirred vigorously for 20 min, and the phases were allowed to separate (10 h). The organic phase was collected, and the aqueous phase was combined with MTBE (9.44 kg), stirred for 15 min, and allowed to settle (45 min). The organic phase was collected, and the aqueous phase was combined with MTBE (9.44 kg), stirred for 15 min, and allowed to settle (15 min). The three organic phases were combined and washed three times with 1N hydrochloric acid (8.44 kg portions) and once with water (6.39 kg), using 15 min of stirring and 15 min of settling time for each wash. The resulting solution was dried over anhydrous sodium sulfate (2.0 kg) and filtered. The filtrate was concentrated under reduced pressure at 31° C. (2 h) to give an solid. This solid was heated under vacuum for 4 h at 39° C. for 4 h and for 16 h at 25° C., leaving 704 g (81%) of 5 (99.7% purity by GC).

Procedure C (streamlined synthesis of 5, using 2 as starting material): A stirred mixture of sodium ethoxide in ethanol (21 weight percent, 343 g, 1.05 mol), ethanol (anhydrous, 300 mL) and diethyl malonate (168 g, 1.05 mol) was heated to 40° C. for 1.5 h. To this mixture was added a solution of (R)-tert-butyl 3-(methylsulfonyloxy)pyrrolidine-1-carboxylate (138 g, 0.592 mol) in ethanol (100 mL) and the reaction mixture was heated to 78° C. for 8 h. The cooled reaction mixture was diluted with water (2.0 L) and acidified to pH=3 with 6M HCl (100 mL). The aqueous ethanol mixture was extracted with toluene (1.0 L), and the organic phase concentrated under vacuum to afford 230 g of a red oil. The red oil was added at 85° C. to a 22.5 weight percent aqueous potassium hydroxide (748 g, 3.01 mol). After the addition was complete, the reaction temperature was allowed to slowly rise to 102° C. while a distillation of ethanol ensued. When the reaction temperature had reached 102° C., and distillation had subsided, heating was continued for an additional 90 min. The reaction mixture was cooled to ambient temperature and washed with toluene (2×400 mL). To the aqueous layer was added 600 mL 6M hydrochloric acid, while keeping the internal temperature below 20° C. This resulted in the formation of a precipitate, starting at pH of about 4-5. The suspension was filtered, and the filter cake was washed with 300 mL water. The solid was dried under vacuum to afford 77 g of (R)-2-(1-(tert-butoxycarbonyl)pyrrolidin-3-yl)malonic acid as an off-white solid (54% yield with respect to (R)-tert-butyl 3-(methylsulfonyloxy)pyrrolidine-1-carboxylate). $^1$H NMR (DMSO-$d_6$, 400 MHz): δ 3.47 (m, 1H); 3.32 (m, 1H); 3.24 (m, 1H); 3.16 (m, 1H); 3.92 (m, 1H); 2.86 (m, 1H); 1.95 (m, 1H); 1.59 (m, 1H); 1.39 (s, 9H).

A suspension of (R)-2-(1-(tert-butoxycarbonyl)pyrrolidin-3-yl)malonic acid (15 g, 55 mmol) in toluene (150 mL) and dimethylsulfoxide (2 mL) was heated to reflux for a period of 2 h. The mixture was allowed to reach ambient and diluted with MTBE (150 mL). The organic solution was washed with 10% aqueous citric acid (2×200 mL), and the solvent was removed under vacuum to afford 11.6 g of (R)-2-(1-(tert-butoxycarbonyl)-pyrrolidin-3-yl)acetic acid as an off-white solid (92% yield). $^1$H NMR (DMSO-$d_6$, 400 MHz): δ 12.1 (s, 1H); 3.36-3.48 (m, 1H); 3.20-3.34 (m, 1H); 3.05-3.19 (m, 1H; 2.72-2.84 (m, 1H); 2.30-2.42 (m, 1H), 2.22-2.30 (m, 2H); 1.85-2.00 (m, 1H); 1.38-1.54 (m, 1H), 1.35 (2, 9H).

Example 6

Synthesis of tert-butyl(R)-3-(2-hydroxyethyl)pyrrolidine-1-carboxylate (6)

Procedure A: A solution of (R)-2-(1-(tert-butoxycarbonyl)pyrrolidine-3-yl)acetic acid (49.0 g, 214 mmol) in tetrahydrofuran (THF) (200 mL) was cooled to −10° C. 250 mL (250 mmol) of a 1M borane in THF solution was added slowly to the flask while maintaining the temperature lower than 0° C. The solution was warmed to ambient temperature and stirred for 1 h. The solution was sampled hourly and analyzed by HPLC to establish completion of the reaction. Upon completion of the reaction, the solution was cooled to 0° C., and a 10% sodium hydroxide solution (80 mL) was added dropwise over a 30 minute period to control gas evolution. The solution was extracted with 500 mL of a 1:1 hexanes/ethyl acetate solution. The organic layer was washed with saturated sodium chloride solution and dried with 10 g of silica gel. The silica gel was removed by filtration and washed with 100 mL of 1:1 hexanes/ethyl acetate. The organic layers were combined and concentrated under vacuum to give 6 (42 g, 91.3%) as a light-orange oil that solidified upon sitting. $^1$H NMR (CDCl$_3$, 400 MHz) δ 3.67 (m, 2H), 3.38-3.62 (m, 2H), 3.25 (m, 1H), 2.90 (m, 1H), 2.25 (m, 1H), 1.98-2.05 (m, 1H), 1.61-1.69 (m, 2H), 1.48-1.59 (m, 2H), 1.46 (s, 9H).

Procedure B: Borane-THF complex (3.90 kg or L of 1M in THF, mol) was added slowly to a stirred solution of (R)-2-(1-(tert-butoxycarbonyl)pyrrolidine-3-yl)acetic acid (683 g, 3.03 mol) in THF (2.5 kg), kept under nitrogen gas, and using a water bath to keep the temperature between 23 and 28° C. The addition took 1.75 h. Stirring at 25° C. was continued for 1 h, after which time GC analysis indicated complete reaction. The reaction mixture was cooled to <10° C. and maintained below 25° C. as 10% aqueous sodium hydroxide (1.22 kg) was slowly added. The addition took 40 min. The mixture was stirred 1 h at 25° C., and then combined with 1:1 (v/v) heptane/ethyl acetate (7 L). The mixture was stirred for 15 min and allowed to separate into phases (1 h). The organic phase was withdrawn, and the aqueous phase was combined with a second 7 L portion of 1:1 heptane/ethyl acetate. This was stirred for 15 min and allowed to separate into phases (20 min). The organic phase was again withdrawn, and the combined organic phases were washed with saturate aqueous sodium chloride (4.16 kg), using 15 min of mixing and 1 h of settling time. The organic phase was combined with silica gel (140 g) and stirred 1 h. The anhydrous sodium sulfate (700 g) was added, and the mixture was stirred for 1.5 h. The mixture was filtered, and the filter cake was washed with 1:1 heptane/ethyl acetate (2 L). The filtrate was concentrated under vacuum at <40° C. for 6 h. The resulting oil weighed 670 g (103% yield) and contains traces of heptane, but is otherwise identical to previously prepared samples of 6, by NMR analysis.

Example 7 tert-butyl(R)-3-(2-(methylsulfonyloxy)ethyl)pyrrolidine-1-carboxylate (7)

Procedure A: To a solution of tert-butyl(R)-3-(2-hydroxymethyl)pyrrolidine-1-carboxylate (41.0 g, 190 mmol)) was added triethylamine (40 mL) in toluene (380 mL) and cooled to −10° C. Methanesulfonyl chloride (20.0 mL, 256 mmol) was added slowly so as to maintain the temperature around −5 to 0° C. The solution was warmed to ambient temperature and stirred for 1 h. The solution was sampled hourly and analyzed by HPLC to establish completion of the reaction. Upon completion of reaction, the solution was filtered, and the filtrate was washed with a 5% sodium bicarbonate solution (250 mL). The organic layer was collected and washed with a saturated aqueous sodium chloride solution (250 mL). The organic layer was collected, dried over silica gel (10 g), and concentrated under vacuum to give 7 (53.0 g, 92.8%) as a light-yellow viscous oil. $^1$H NMR (CDCl$_3$, 400 MHz) δ 4.26 (t, J=6.8 Hz, 2H), 3.41-3.63 (m, 2H),3.27 (m, 1H), 3.02 (s, 3H), 2.92 (m, 1H), 2.28 (m, 1H), 2.05 (m, 1H), 1.83 (m, 2H), 1.50-1.63 (m, 1H), 1.46 (s, 9H).

Procedure B: Under a nitrogen atmosphere, a solution of triethylamine (460 g, 4.55 mol) and tert-butyl(R)-3-(2-hydroxymethyl)pyrrolidine-1-carboxylate (the entire sample from Example 7, Procedure B, 3.03 mol) in toluene (5.20 kg) was stirred and cooled to 5° C. Methanesulfonyl chloride (470 g, 4.10 mol) was added slowly, over a 1.25 h, keeping the temperature below 15° C. using ice bath cooling. The mixture was gradually warmed (over 1.5 h) to 35° C., and this temperature was maintained for 1.25 h, at which point GC analysis indicated that the reaction was complete. The mixture was cooled to 25° C., and solids were filtered off and the filter cake washed with toluene (1.28 kg). The filtrate was stirred with 10% aqueous sodium bicarbonate (4.0 kg) for 15 min, and the phases were allowed to separate for 30 min. The organic phase was then stirred with saturated aqueous sodium chloride (3.9 kg) for 30 min, and the phases were allowed to separate for 20 min. The organic phase was combined with silica gel (160 g) and stirred for 1 h. Anhydrous sodium sulfate (540 g) was added, and the mixture was stirred an additional 40 min. The mixture was then filtered, and the filter cake was washed with toluene (460 g). The filtrate was concentrated under vacuum at 50° C. for 5 h, and the resulting oil was kept under vacuum at 23° C. for an additional 8 h. This left 798 g of 7, 93% pure by GC analysis.

Example 8

Synthesis of tert-butyl(R)-3-vinylpyrrolidine-1-carboxylate (9)

Procedure A: A solution of tert-butyl(R)-3-((methylsulfonyloxy)ethyl)pyrrolidine-1-carboxylate (49.0 g, 167 mmol), sodium iodide (30.0 g, 200 mmol) and 1,2-dimethoxyethane (450 mL) was stirred at 50-60° C. for 4 h. The solution was sampled hourly and analyzed by HPLC to establish completion of the reaction. Upon completion of reaction, the solution was cooled to −10° C., and solid potassium tert-butoxide (32.0 g, 288 mmol) was added while maintaining temperature below 0° C. The reaction mixture was warmed to ambient temperature and stirred for 1 h. The mixture was sampled hourly and analyzed by HPLC to establish completion of the reaction. Upon completion of reaction, the mixture was filtered through a pad of diatomaceous earth (25 g dry basis). The cake was washed with 1,2-dimethoxyethane (100 mL). The combined filtrates were concentrated under vacuum, to yield an orange oil with suspended solids. The oil was dissolved in hexanes (400 mL), stirred for 30 min, and filtered to remove the solids. The organic layer was dried over silica gel (10 g), and concentrated under vacuum to give 9 (26.4 g, 82.9%) as a colorless oil. $^1$H NMR (CDCl$_3$, 400 MHz) δ 5.77 (m, 1H), 5.10 (dd, J=1.2 Hz, J=16 Hz, 1H), 5.03 (dd, J=1.2 Hz, J=8.8 Hz, 1H), 3.41-3.59 (m, 2H), 3.29 (m, 1H), 3.05 (m, 1H), 2.78 (m, 1H), 2.01 (m, 1H), 1.62-1.73 (m, 1H), 1.46 (m, 9H).

Procedure B: A solution of tert-butyl(R)-3-(2-(methylsulfonyloxy)ethyl)pyrrolidine-1-carboxylate (792 g of the product of Example 7, Procedure B, ~2.5 mol), sodium iodide (484 g, 3.27 mol) and 1,2-dimethoxyethane (7.2 L) was stirred at 55° C. for 4.5 h under nitrogen, at which time GC analysis indicated that the reaction was complete. The solution was cooled to <10° C., and solid potassium tert-butoxide (484 g, 4.32 mol) was added in portions (1.25 h addition time) while maintaining temperature below 15° C. The reaction mixture was stirred 1 h at 5° C., warmed slowly (6 h) to 20° C., and stirred at 20° C. for 1 h. The solution was filtered through a pad of diatomaceous earth (400 g dry basis). The filter cake was washed with 1,2-dimethoxyethane (1.6 kg). The combined filtrates were concentrated under vacuum, and the semisolid residue was stirred with heptane (6.0 L) for 2 h. The solids were removed by filtration (the filter cake was washed with 440 mL of heptane), and the filtrate was concentrated under vacuum at 20° C. to give 455 g of 9 (90.7% pure). A sample of this material (350 g) was fractionally distilled at 20-23 torr to give 296 g of purified 9 (bp 130-133° C.) (>99% pure by GC analysis).

Example 9

Synthesis of 3-bromo-5-(tetrahydro-2H-pyran-4-yloxy)pyridine (12)

A solution of 5-bromopyridin-3-ol (146 g, 834 mmol), tetrahydro-2H-pyran-4-ol (128 g, 1250 mmol), and triphenylphosphine (329 g, 1250 mmol) in toluene (2.0 L) was heated to reflux, and 750 mL of distillate was removed via a Dean-Stark trap. The reaction mixture was cooled to 60° C., and 547 g (1.25 mol) of a 40% (w/w) solution of DEAD in toluene was added drop-wise over a 1 hour period. The addition was exothermic with the reactor temperature at the end of addition near 95° C. The reaction mixture was stirred at 115° C. for 18 h, and a portion of the reaction solution was sampled and analyzed by HPLC to establish that the reaction was complete. Upon completion of reaction, 500 mL of solvent was removed by distillation, and the pot residue was cooled to ambient temperature. This organic layer was washed with 10% aqueous sodium hydroxide (2×0.50 L) and concentrated under vacuum to produce a viscous oil, which was dissolved in 2N hydrochloric acid (1.0 L). Diatomaceous earth (100 g) was added with stirring and the resulting suspension was filtered. The pad was rinsed with 2N hydrochloric acid (1.0 L), and the filtrates were combined and extracted with diisopropyl ether (500 mL). The diisopropyl ether layer was discarded, and the aqueous layer was treated with carbon black (10 g) and stirred at 45-50° C. for 1 h. The suspension was filtered through a pad of diatomaceous earth (25 g). The filtrate was collected, cooled to 5° C., and the pH adjusted with 50% aqueous sodium hydroxide (250 mL) to pH=13. The solution was extracted twice with chloroform (1.0 L, 600 mL), and the chloroform extracts were combined and concentrated under vacuum to give 12 as a dark red viscous oil/low melting solid (187 g, 87%), which was used without further purification. $^1$H NMR (CDCl$_3$, 400 MHz) δ 8.29 (s, 1H), 8.24 (s, 1H), 7.38 (s, 1H), 4.52 (m, 1H), 3.98 (m, 2H), 3.60 (m, 2H), 2.05 (m, 2H), 1.81 (m, 2H).

Example 10

Synthesis of tert-butyl(R)-(E)-3-(2-(5-(tetrahydro-2H-pyran-4-yloxy)pyridin-3-yl)vinyl)pyrrolidine-1-carboxylate (13)

A mixture of tert-butyl(R)-3-vinylpyrrolidine-1-carboxylate 9 (7.00 g, 35.5 mmol), 3-bromo-5-(tetrahydro-2H-pyran-4-yloxy)pyridine 12 (10.0 g, 38.8 mmol), palladium acetate (0.40 g, 1.8 mmol), tricyclohexylphosphine (1.0 g, 3.57 mmol) and diisopropylethylamine (15 mL) in 1-methyl-2-pyrrolidinone (130 mL) was stirred at 130° C. for 17 h. The reaction was cooled to ambient temperature, diluted with water (800 mL) and extracted with ethyl acetate (2×200 mL). The combined organic extracts were dried over sodium sulfate, concentrated, and purified by silica gel column chromatography using 60-100% ethyl acetate in hexanes. This product was further purified on reverse phase HPLC using 0.05% trifluoroacetic acid in acetonitrile and 0.05% trifluoroacetic acid in water to obtain tert-butyl(R)-(E)-3-(2-(5-(tetrahydro-2H-pyran-4-yloxy)pyridin-3-yl)vinyl)pyrrolidine-1-carboxylate (11.0 g) as a gum. $^1$H-NMR (CDCl$_3$, 400 MHz): δ 8.41 (s, 1 H), 8.37 (d, J=2.3 Hz, 1 H), 7.68 (s, 1 H), 6.48 (d, J=16.1 Hz, 1 H), 6.43 (dd, J=16.0, 6.4 Hz, 1 H), 4.71-4.66 (m, 1 H), 4.02-3.96 (m, 2 H), 3.68-3.52 (m, 4 H), 3.44-3.34 (m, 1 H), 3.28-3.15 (m, 1 H), 3.09-2.98 (m, 1 H), 2.18-2.04 (m, 3 H), 1.90-1.78 (m, 3 H), 1.48 (s, 9 H)

Example 11

Synthesis of (R)-3-((E)-2-(pyrrolidin-3-yl)vinyl)-5-(tetrahydropyran-4-yloxy)pyridine (14) Hemigalactarate A solution of tert-butyl(R)-(E)-3-(2-(5-(tetrahydro-2H-pyran-4-yloxy)pyridin-3-yl)vinyl)pyrrolidine-1-carboxylate (18 g, 48.13 mmol) in dichloromethane (40 mL) and trifluoroacetic acid (40 mL) was stirred at ambient temperature for 2 h. The reaction was concentrated on a rotary evaporator, and the residue was partitioned between saturated sodium chloride (50 mL) and chloroform (100 mL). The mixture was basified to pH 9 with 10% aqueous sodium hydroxide solution. The organic layer was separated and the aqueous layer extracted with chloroform (2×100 mL). The combined organic layers were dried over sodium sulfate and concentrated on a rotary evaporator to give (R)-3-((E)-2-(pyrrolidin-3-yl)vinyl)-5-(tetrahydro-2H-pyran-4-yloxy)pyridine (8.0 g) as a gum. This was dissolved in methanol (100 mL) and galactaric acid (3.0 g, 14.6 mmol) was added and the mixture was heated to reflux. This hot solution was filtered, and filtrate was allowed to cool to ambient temperature. The crystallized product was filtered and solid was suspended in 10% water in ethanol (180 mL). The suspension was heated to reflux and hot solution was filtered. The filtrate was allowed to cool to ambient temperature. Crystallized product was filtered and dried on high vacuum pump to give (R)-3-((E)-2-pyrrolidin-3-ylvinyl)-5-(tetrahydro-2H-pyran-4-yloxy)pyridine hemigalactarate (4.5 g). MP: 179° C. $^1$H-NMR (CD$_3$OD, 300 MHz): δ 8.04 (s, 1 H), 8.01 (d, J=2.2 Hz, 1 H), 7.36 (s, 1 H), 6.46 (d, J=16.0 Hz, 1 H), 6.21 (dd, J=16.0, 7.5 Hz, 1 H), 4.65-4.54 (m, 1 H), 4.12 (s, 1 H), 3.89-3.83 (m, 2 H), 4.80 (s, 1 H), 3.56-3.33 (m, 4 H), 3.27-3.18 (m, 1 H), 3.12-2.96 (m, 2 H), 2.23-2.14 (m, 1 H), 1.98-1.91 (m, 2 H), 1.88-1.78 (m, 1 H), 1.68-1.58 (m, 2 H); MS (m/z): 275 (M+1).

Example 12

Large Scale Synthesis of (R)-3-((E)-2-(pyrrolidin-3-yl)vinyl)-5-(tetrahydropyran-4-yloxy)pyridine (14) mono-L-malate Under a nitrogen atmosphere, a mixture of 3-bromo-5-(tetrahydro-2H-pyran-4-yloxy)pyridine (125 g of 85% purity, 410 mmol), (R)-tert-butyl-3-vinylpyrrolidine-1-carboxylate (67.4 g, 340 mmol), palladium(II) acetate (8.1 g, 36 mmol), tri-n-butylphosphine (15 g, 74 mmol), potassium carbonate (74.0 g, 530 mmol), and DMAC (0.85 L) was stirred and heated at 130° C., monitoring for completion of reaction by LCMS. Upon completion of reaction, the reaction mixture was cooled to ambient temperature and filtered through a pad of diatomaceous earth (50 g dry basis), washing the pad with diisopropyl ether (0.60 L). The filtrate was combined with diisopropyl ether (0.60 L) and de-ionized water (0.50 L) and mixed for 15 min. The phases were allowed to separate (15 min), and the organic phase was collected. The aqueous phase was extracted with a second portion of diisopropyl ether (0.60 L), using 15 min of mixing and 15 min of settling time. The combined diisopropyl ether layers were washed with deionized water (2×0.50 L) and concentrated under reduced pressure to produce a dark red viscous oil (136 g). This oil was dissolved in diisopropyl ether (1.40 L) and cooled to around 10° C. with an ice bath before charging 6N hydrochloric acid (0.40 L) via a dropping addition funnel over a 15 min period, keeping the temperature below 20° C. The biphasic mixture was warmed to ambient temperature (off-gassing occurred as it warmed) and stirred until LCMS indicated that the reaction was complete. Upon completion of reaction, the phases were allowed to separate, and the organic layer was discarded. The pH of the aqueous layer was adjusted to pH 5-6 using 10% aqueous sodium hydroxide (0.485 L) and extracted with chloroform (0.25 L). The chloroform layer was discarded. The aqueous layer was then adjusted to pH>13 using 10% aqueous sodium hydroxide (0.075 L) and again extracted with chloroform (0.50 L). The chloroform extract was concentrated under reduced pressure to yield a red, viscous oil (55.0 g). This material was a mixture of the desired (R)-3-((E)-2-(pyrrolidin-3-yl)vinyl)-5-tetrahydro-2H-pyran-4-yloxy)pyridine (~75%) and the corresponding Z (~5%) and "exo" (~20%) isomers by NMR analysis. This result was reproducible over multiple runs.

The Z and "exo" impurities were removed from the desired (R)-3-((E)2-(pyrrolidin-3-yl)vinyl)-5-tetrahydro-2H-pyran-4-yloxy)pyridine by conversion to the oxalate salt. A solution of oxalic acid (53.2 g. 591 mmol) in a mixture of 2-propanol (0.20 L) and de-ionized water (0.09 L) was prepared by stirring and heating at 50-55° C. (15 min). This solution was added, over a 5 min period, to a stirred solution of (R)-3-((E)-2-(pyrrolidin-3-yl)vinyl)-5-tetrahydro-2H-pyran-4-yloxy) pyridine (82.0 g of 76% pure by HPLC, 299 mmol) in 2-propanol (1.0 L) held at 70-75° C. The oxalic acid addition produced an exotherm (4-5° C.) that was controlled by adjusting the rate of addition. The heating source was removed and the solution was cooled slowly to 45-50° C. over 45 min. A precipitate formed quickly, beginning around 65-70° C. and becoming heavier as the resulting suspension cooled. The solids were collected by filtration at 45-50° C. and washed successively with 2-propanol (2×0.25 L) and hexanes (2×0.20 L). The tan solid was air dried for 2 h, after which it weighed (95 g). NMR analysis indicated that the content of the Z and "exo"impurities had each been reduced to <1%. This result was reproducible over multiple runs. Material of even greater purity was obtained by recrystallization from ethanol/water. The stoichiometry of the salt was 2.3:1 acid/base (see Example 15).

A solution of (R)-3-((E)-2-(pyrrolidinium-3-yl)vinyl)-5-(tetrahydro-2H-pyran-4-yloxy)pyridinium oxalate (380 g) in de-ionized water (2.6 L) was stirred and cooled to around 10° C. with an ice bath. Aqueous sodium hydroxide (0.40 L of 25%) was added over a period of 15 min, keeping the temperature below 30° C. Chloroform (1.6 L) was then added, and the mixture was stirred vigorously for 20 min and filtered to remove insoluble sodium oxalate. The layers were allowed to separate, and the chloroform layer was combined with Silicycle Si-Thiol® (21.6 g). The mixture was stirred and heated at 50-55° C. for 3-4 h, cooled to ambient temperature and filtered. The filtrate was concentrated under reduced pressure to produce a light red viscous oil (221 g). A portion of this free base (216 g) was dissolved in 2-propanol (1.2 L), heated to 70-75° C. and treated with solid L-malic acid (106 g), using a 2-propanol rinse (100 mL) to aid transfer. Dissolution of the solid produced an exotherm of 5-7° C. over 3-5 min. The mixture was kept at 75-78° C. for 10 min, to ensure complete dissolution of the solids, and then cooled slowly to ambient temperature (90 min). As the temperature approached 65° C., the solution was seeded with a few crystals of (R)-3-((E)-2-(pyrrolidin-3-yl)vinyl)-5-(tetrahydro-2H-pyran-4-yloxy)pyridine mono-L-malate salt. After stirring at ambient temperature for 1 h, the suspension was filtered. The collected solids were washed with 2-propanol (2×0.80 L), air dried for 30 minutes, and vacuum dried at 78° C. for 8 h. The resulting off-white material weighed 297 g and was >99% pure by HPLC.

Example 13

Procedure for Screening for Salt Forms of (R)-3-((E)-2-(pyrrolidin-3-yl)vinyl)-5-(tetrahydropyran-4-yloxy)pyridine Test tubes (4 mL), provided with magnetic stir bars, were charged with equi-milimolar amounts of (R)-3-((E)-2-(pyrrolidin-3-yl)vinyl)-5-(tetrahydropyran-4-yloxy)pyridine base and the acid of interest (neat) and dissolved with 500 μL of either 2-propanol or acetonitrile with the aid of heat. If precipitation did not occur upon cooling, isopropyl acetate (100 μL) was added as an anti-solvent.

If no precipitation occurred, the solvent was evaporated under a nitrogen stream with moderate heating and an alternative solvent was tried. Alternative solvents included acetone, ethyl acetate, isopropyl acetate, absolute ethanol, acetonitrile, hexane, tert-butanol, tert-butyl acetate, and blends thereof.

The use of alcohols was avoided in the case of sulfonic acids. Isopropyl acetate was used cautiously, while the use of acetone and ethyl acetate was discontinued due to demonstrated reactivity of the secondary amine function of (R)-3-((E)-2-pyrrolidin-3-ylvinyl)-5-(tetrahydro-2H-pyran-4-yloxy)pyridine with these solvents.

Results of these experiments are summarized in Table 1.

TABLE 1

Acids used in preliminary salt screen

| Acid | Result |
| --- | --- |
| 4-Acetamidobenzoic | oil |
| Adipic | oil |
| (1 R,3S)-(+)-Camphoric | oil |
| (1 S)-(+)-1 O-Camphorsulfonic | oil |
| Citric | tacky gum |
| Fumaric | oil |
| D-glucuronic | brown gum |
| Hydrochloric | red oil |
| 4-Hydroxybenzoic | tacky gum |
| 1-Hydroxy-2-naphthoic (Xinafoic) | brown gum |
| Maleic | Oil |
| L-Malic | Crystals |
| Malonic | Oil |
| (R)-Mandelic | Oil |
| (S)-Mandelic | Oil |
| Methanesulfonic | Oil |
| 4-Methoxybenzoic | Oil |
| Phosphoric | Gum |
| Succinic | red oil |
| L-Tartaric | Oil |
| p-Toluenesulfonic•H20 | Oil |

As demonstrated in Table 1, finding solid salt forms for (R)-3-((E)-2-pyrrolidin-3-ylvinyl)-5-(tetrahydro-2H-pyran-4-yloxy)pyridine was challenging. Reported below are examples of solids salts and their syntheses.

Example 14

Preparation of (R)-3-((E)-2-(pyrrolidin-3-yl)vinyl)-5-(tetrahydropyran-4-yloxy)pyridine mono-L-malate To a stirred solution of (R)-3-((E)-2-(pyrrolidin-3-yl)vinyl)-5-(tetrahydropyran-4-yloxy)pyridine (900 mg; 3.28 mmol) in 2-propanol (5 mL), heated to near boiling, was added L-malic acid (439.8 mg; 3.28 mmol, neat) in three portions. The solution was stirred near boiling for 10 min. Isopropyl acetate (1 mL) was added, heating was discontinued, and the solution was seeded while still hot. The solution was allowed to cool to ambient temperature (22° C.) with stirring whereupon the salt precipitated as a white granular solid. The salt was re-dissolved by heating, re-seeded while hot, cooled and allowed to stand at ambient temperature without stirring for 24 h. The resulting plate-like crystals were collected by suction filtration, washed with isopropyl acetate (5 mL), and dried under nitrogen for 10 min. Further drying in vacuum oven at 70° C. for 1.5 h afforded 1.267 g (94.6%) of light-yellow crystals (m.p.=118-119° C.). $^1$H-NMR (D$_2$O or d$_6$-DMSO) is consistent with a 1:1 acid:base stoichiometry. DSC exhibits a single endotherm with maxima at 119.62° C. DVS shows minimum water uptake up to 80% R.H. $^1$H-NMR (D$_2$O, 400 MHz): δ 8.15 (s, 1 H), 8.10 (s, 1 H), 7.58 (s, 1 H), 6.52 (d, 1 H), 6.28 (dd, 1 H), 4.63 (m, 1 H, partially masked by residual H2O resonance), 4.22 (dd, 1 H), 3.88 (m, 2 H), 3.55 (m, 2 H), 3.46 (dd, 1 H), 3.38 (m, 1 H), 3.25 (m, 1 H), 3.11 (m, 1 H), 3.02 (m, 1 H), 2.65 (dd, 1 H), 2.42 (dd, 1 H), 2.20 (m, 1 H), 1.96 (m, 2 H), 1.85 (m, 1 H), 1.68 (m, 2 H). $^1$H-NMR (d$_6$-DMSO, 400 MHz): δ 8.20 (s, 1 H), 8.18 (s, 1 H), 7.52 (s, 1 H), 6.55 (d, 1 H), 6.46 (dd, 1 H), 4.68 (m, 1 H), 3.87 (m, 3 H), 3.49 (m, 2 H), 3.40 (dd, 1 H), 3.32 (m, 1 H), 3.18 (m, 1 H), 3.05 (m, 1 H), 2.93 (m, 1 H), 2.51 (dd, 1 H, partially masked by residual DMSO), 2.31 (dd, 1 H), 2.14 (m, 1 H), 1.98 (m, 2 H), 1.80 (m, 1 H), 1.58 (m, 2 H).

Example 15

Preparation of (R)-3-((E)-2-(pyrrolidin-3-yl)vinyl)-5-(tetrahydropyran-4-yloxy)pyridine oxalate A warm solution of (1.137 g of 85%, 3.52 mmol corrected for purity) in 2-propanol (8.5 mL) and water (0.4 mL) was treated with oxalic acid (0.373 g, 4.14 mmol), as a solid, in one portion. The resulting mixture was stirred and heated to near reflux. A few solids began to precipitate from the hot solution. The mixture was allowed to cool to ambient temperature. The off-white solids were filtered (Büchner), washed with 2-propanol (10 mL, 8 mL) and dried under vacuum (with an air bleed) at 50° C. for 3 h to yield 0.861 g (50.8% yield based upon a 2.3 oxalate stoichiometry, corrected for purity of the starting material) of an off-white powder. A 0.765 g sample of this material was recrystallized from a mixture of 2-propanol (8 mL) and water (1.3 mL), heated at reflux. Upon cooling to ambient temperature, the resulting solids were filtered (Büchner), washed with 2-propanol (10 mL), dried under vacuum (with an air bleed) at 50° C. for 4 h and then further vacuum dried with an air bleed) at 70° C. for 24 h to afford 0.441 g (57.6% recovery) of an off-white to white solid, mp 180-181° C. Cacl'd for C$_{16}$H$_{22}$N$_2$O$_2$.2.3C$_2$H$_2$O$_4$: C, 51.39; H, 5.57; N, 5.82. Found: C, 51.09, 51.24; H, 5.67, 5.66; N, 5.84, 5.92.

$^1$H-NMR (D$_2$O, 400 MHz) δ 8.23 (s, 1 H), 8.20 (s, 1 H), 7.96 (s, 1 H), 6.54 (d, 1 H), 6.40 (dd, 1 H), 4.73 (m, 1 H), 3.84 (m, 2 H), 3.54 (m, 2 H), 3.45 (dd, 1 H), 3.35 (m, 1 H), 3.23 (m, 1 H), 3.12 (m, 1 H), 3.02 (m, 1 H), 2.16 (m, 1 H), 1.96 (m, 2 H), 1.83 (m, 1 H), 1.68 (m, 2 H).

Example 16

Preparation of (R)-3-((E)-2-(pyrrolidin-3-yl)vinyl)-5-(tetrahydropyran-4-yloxy)pyridine di-p-toluoyl-D-tartrate To a stirred solution of (R)-3-((E)-2-(pyrrolidin-3-yl)vinyl)-5-(tetrahydropyran-4-yloxy)pyridine (4.0 g, 15 mmol) in ethanol (12.5 mL) solution, heated to 60° C., was added solid di-p-toluoyl-D-tartaric acid (5.3 g, 14 mmol). The solution was held at 60° C. for 2-3 min to ensure complete dissolution of the solids, then the heat source was removed and the solution was cooled to 25-30° C. over 60 min. The resulting suspension was held at 25-30° C. for 30 min, and then filtered to collect the solids. The solids were washed with ethanol (2×20 mL), air dried for 30 min, then dried in a vacuum oven under reduced pressure at 50° C., until a constant weight was established, to give (R)-3-((E)-2-(pyrrolidin-3-yl)vinyl)-5-

(tetrahydropyran-4-yloxy)pyridine di-p-toluoyl-D-tartrate as an off-white solid (6.7 g, 72%). NNNMR analysis indicated a 1:1 salt stoichiometry. $^1$H-NMR (DMSO-$d_6$, 400 MHz) δ 8.18 (s, 1 H), 8.15 (s, 1 H), 7.86 (d, 4 H), 7.47 (s, 1 H), 7.32 (d, 4 H), 6.43 (d, 1 H), 6.36 (m, 1 H), 5.67 (s, 2 H), 4.69 (m, 1 H), 3.85 (m, 2 H), 3.49 (m, 2 H), 3.25 (m, 2 H), 3.10 (m, 1 H), 2.88 (m, 2 H), 2.39 (s, 6 H), 1.98 (m, 3 H), 1.60 (m, 3 H).

Biological Assays

Example 17

Radioligand Binding at CNS nAChRs: α4β2 NNR Subtype

Preparation of membranes from rat cortex: Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, and then decapitated. Brains were removed and placed on an ice-cold platform. The cerebral cortex was removed and placed in 20 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the suspension was homogenized by Polytron. The homogenate was centrifuged at 18,000×g for 20 min at 4° C. and the resulting pellet was re-suspended in 20 volumes of ice-cold water. After 60 min incubation on ice, a new pellet was collected by centrifugation at 18,000×g for 20 min at 4° C. The final pellet was re-suspended in 10 volumes of buffer and stored at −20° C.

Preparation of membranes from SH-EP1/human α4β2 clonal cells: Cell pellets from 40 150 mm culture dishes were pooled, and homogenized by Polytron (Kinematica GmbH, Switzerland) in 20 milliliters of ice-cold preparative buffer. The homogenate was centrifuged at 48,000 g for 20 min at 4° C. The resulting pellet was re-suspended in 20 mL of ice-cold preparative buffer and stored at −20° C.

Assay. On the day of the assay, the frozen membranes were thawed and spun at 48,000×g for 20 min. The supernatant was decanted and discarded. The pellet was resuspended in Dulbecco's phosphate buffered saline (PBS, Life Technologies) pH 7.4 and homogenized with the Polytron for 6 seconds. Protein concentrations were determined using a Pierce BCA Protein Assay Kit, with bovine serum albumin as the standard (Pierce Chemical Company, Rockford, Ill.).

Membrane preparations (approximately 50 μg for human and 200-300 μg protein for rat α4β2) were incubated in PBS (50 μL and 100 μL respectively) in the presence of competitor compound (0.01 nM to 100 μM) and 5 nM [$^3$H]nicotine for 2-3 h on ice. Incubation was terminated by rapid filtration on a multi-manifold tissue harvester (Brandel, Gaithersburg, Md.) using GF/B filters presoaked in 0.33% polyethyleneimine (w/v) to reduce non-specific binding. Tissue was rinsed 3 times in PBS, pH 7.4. Scintillation fluid was added to filters containing the washed tissue and allowed to equilibrate. Filters were then counted to determine radioactivity bound to the membranes by liquid scintillation counting (2200CA Tri-Carb LSC, Packard Instruments, 50% efficiency or Wallac Trilux 1450 MicroBeta, 40% efficiency, Perkin Elmer).

Data were expressed as disintegrations per minute (DPMs). Within each assay, each point had 2-3 replicates. The replicates for each point were averaged and plotted against the log of the drug concentration. $IC_{50}$, which is the concentration of the compound that produces 50% inhibition of binding, was determined by least squares non-linear regression. Ki values were calculated using the Cheng-Prussof equation (1973):

$$Ki = IC_{50}/(1 + N/Kd)$$

where N is the concentration of [$^3$H]nicotine and Kd is the affinity of nicotine (3 nM, determined in a separate experiment).

Example 18

Radioligand Binding at CNS nAChRs: α7 NNR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, and then decapitated. Brains were removed and placed on an ice-cold platform. The hippocampus was removed and placed in 10 volumes (weight:volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 2 mg protein/mL. Protein was determined by the method of Lowry et al., *J. Biol. Chem.* 193: 265 (1951), using bovine serum albumin as the standard.

The binding of [$^3$H]MLA was measured using a modification of the methods of Davies et al., *Neuropharmacol.* 38: 679 (1999), herein incorporated by reference with regard to such method. [$^3$H]MLA (Specific Activity=25-35 Ci/mmol) was obtained from Tocris. The binding of [$^3$H]MLA was determined using a 2 h incubation at 21° C. Incubations were conducted in 48-well micro-titre plates and contained about 200 μg of protein per well in a final incubation volume of 300 μL. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at ambient temperature. Filters were soaked in de-ionized water containing 0.33% polyethyleneimine to reduce non-specific binding. Each filter was washed with PBS (3×1 mL) at ambient temperature. Non-specific binding was determined by inclusion of 50 μM non-radioactive MLA in selected wells.

The inhibition of [$^3$H]MLA binding by test compounds was determined by including seven different concentrations of the test compound in selected wells. Each concentration was replicated in triplicate. $IC_{50}$ values were estimated as the concentration of compound that inhibited 50 percent of specific [$^3$H]MLA binding. Inhibition constants (Ki values), reported in nM, were calculated from the $IC_{50}$ values using the method of Cheng et al., *Biochem. Pharmacol.* 22: 3099-3108 (1973).

Selectivity vs. Peripheral nAChRs

Example 19

Interaction at the Human Muscle nAChR Subtype

Activation of muscle-type nAChRs was established on the human clonal line TE671/RD, which is derived from an embryonal rhabdomyosarcoma (Stratton et al., *Carcinogen* 10: 899 (1989)). These cells express receptors that have pharmacological (Lukas, *J. Pharmacol. Exp. Ther.* 251: 175 (1989)), electrophysiological (Oswald et al., *Neurosci. Lett.* 96: 207 (1989)), and molecular biological profiles (Luther et al., *J. Neurosci.* 9: 1082 (1989)) similar to the muscle-type nAChR.

TE671/RD cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 12 well polystyrene plates (Costar). Experiments were conducted when the cells reached 100% confluency.

Nicotinic acetylcholine receptor (nAChR) function was assayed using $^{86}Rb^+$ efflux according to the method described by Lukas et al., *Anal. Biochem.* 175: 212 (1988). On the day of the experiment, growth media was gently removed from the well and growth media containing $^{86}$Rubidium chloride ($10^6$ µCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH. 7.4), taking care not to disturb the cells. Next, cells were exposed to either 100 µM of test compound, 100 µM of L-nicotine (Acros Organics) or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 µM L-nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Example 20

Interaction at the Human Ganglionic nAChR Subtype

The cell line SH-SY5Y is a continuous line derived by sequential subcloning of the parental cell line, SK-N-SH, which was originally obtained from a human peripheral neuroblastoma. SH-SY5Y cells express a ganglion-like nAChR (Lukas et al., *Mol. Cell. Neurosci.* 4: 1 (1993)).

Human SH-SY5Y cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 12 well polystyrene plates (Costar). Experiments were conducted when the cells reached 100% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}$Rubidium chloride ($10^6$ µCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4), taking care not to disturb the cells. Next, cells were exposed to either 100 µM of test compound, 100 µM of nicotine, or buffer alone for 4 min. Following the exposure period, the supernatant containing the released $^{86}Rb^+$ was removed and transferred to scintillation vials. Scintillation fluid was added and released radioactivity was measured by liquid scintillation counting Within each assay, each point had 2 replicates, which were averaged. The amount of $^{86}Rb^+$ release was compared to both a positive control (100 µM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

Example 21

Novel Object Recognition

Memory was assessed by using a three-trial novel object recognition test (Luine et al., *Pharm. Biochem. Behav.* 74, 213-220 (2002)). On the first day (exploratory trial), rats were allowed to explore an open arena (44.5×44.5×30.5 cm) for 6 min. On the second day (acquisition trial), rats were allowed to explore the same arena in the presence of two identical objects (both object A) for 3 min. On the third day (retention or recall trial), performance was evaluated by allowing the same animal to re-explore the arena for 3 min in the presence of two different objects: the familiar object A and a novel object B. An inter-trial interval of 24 h was imposed between the three NOR trials. Recognition memory was assessed by comparing the time spent exploring a novel (object B) versus a familiar (object A) object during the recall trial. Recognition index was assessed for each animal and expressed as a ratio ((time B/time A+time B)×100).

Example 22

Radial Arm Maze

Working memory was assessed in a radial arm maze (RAM) task. The RAM task was conducted using an automated eight-arm maze (Med Associates, Inc.) The maze was located on a circular table approximately 88 cm above the floor with overhead lighting in a dedicated testing ambient and large, high contrast geometric shapes on the wall. Furthermore, additional visual cues were located at the hub entry into each arm, above each the food hopper and on the ceiling. The central platform measured 30.5 cm in diameter with eight arms (9 cm W×45.7 cm L×16.8 cm H) radiating from it. Automatic guillotine doors were located at the entrance to each runway with a pellet receptacle at the distal end of each arm. White noise will be audible during all training and testing procedures. Activity on the maze was monitored by tracking quantitative activity (generated by infra-red beam breaks) on the computer interface and monitor screen.

Following the baseline assessment and after re-attainment test session criterion, animals were assessed for their sensitivity to chemically-induced cognitive impairment using the muscarinic antagonist scopolamine (0.2-0.4 mg/kg; s.c.). A dose of scopolamine was determined for each animal based on the minimum dose that produced significant and reliable cognitive impairment. Scopolamine was administered 0.5 h prior to the acquisition phase trial whereas, (R)-3-((E)-2-(pyrrolidin-3-yl)vinyl)-5-(tetrahydropyran-4-yloxy)pyridine hemi-galactarate (0.03 mg/kg; p.o.) was administered 0.5 h prior to the start of the recall (or test) phase trial. In the acquisition trial, one randomly selected arm was blocked with a Plexiglas barrier situated just inside the arm, behind the hub door. The animal was placed in the central hub of the maze with doors down. After approximately 10 sec, doors to the 7 available arms were raised. The first entry to each open arm was reinforced with a sucrose food pellet. The session ended after all 7 available arms were visited or 5 min elapsed. The order of arms visited, reinforcers received, errors (re-entries), time to complete the task, the number of entries and time required to enter 7 available arms and consume food reinforcer were recorded. In the recall trial, all 8 arms were available, however, only the first visit to the previously blocked arm (i.e., the arm that was blocked during the acquisition trial) was reinforced. The session ended once the previously blocked arm was visited and the reinforcer was consumed or 5 min elapsed. For the recall trial, re-entry errors, the number of (incorrect) arms entered prior to choosing the arm that was blocked during the acquisition trial and the time taken to complete the trial was recorded. The delay between the acquisition and test phase trials was 24 h.

Example 23

CYP Inhibition Studies

Inhibition of CYP1A2, CYP2C9, CYP2C19, CYP2D6 and CYP3A4 catalytic activity by (R)-3-((E)-2-(pyrrolidin-3-yl)vinyl)-5-(tetrahydropyran-4-yloxy)pyridine or a slat thereof was assessed using a fluorogenic CYP assay. Probe substrates which fluoresce upon CYP catalyzed oxidation were used to evaluate the degree of inhibition of the test substrate. A single concentration of each probe substrate (at approximately the apparent $K_m$ value) and two different concentrations of (R)-3-((E)-2-(pyrrolidin-3-yl)vinyl)-5-(tetrahydropyran-4-yloxy)pyridine hemigalactarate (2 and 20 µM) were tested in duplicate. Fluorescence intensity at selected wavelengths was used as a measure of enzyme activity. Decreased fluorescence in the presence of (R)-3-((E)-2-(pyrrolidin-3-yl)vinyl)-5-(tetrahydropyran-4-yloxy)pyridine or a sat thereof was an indication of inhibition. Positive controls (known inhibitors) wlere run concurrently to demonstrate method control and CYP activity. Duplicate samples were run alongside the positive and negative controls. Incubation of test samples was performed at 37° C. Experimental parameters are outlined in Table 2.

TABLE 2

Experiment conditions for fluorescence CYP inhibition assays

| | CYP1A2 | CYP2C9 | CYP2C19 | CYP2D6 | CYP3A4 |
|---|---|---|---|---|---|
| Enzyme amount (pmol/well) | 1 | 2 | 2 | 3 | 1 |
| Probe Substrate | 3 µM CEC | 75 µM MFC | 100 µM MFC | 20 µM MAMC | 15 µM BFC |
| KPO4 pH 7.4 | 0.1M | 0.05M | 0.05M | 0.1M | 0.1M |
| NADPH conc. | 1 mM | 1 mM | 1 mM | 0.06 mM | 1 mM |
| Incubation time | 20 min | 50 min | 40 min | 35 min | 30 min |
| Ex/Em λ (nm) | 405/460 | 405/530 | 405/530 | 390/460 | 405/530 |
| Gain | 20 | 40 | 30 | 10 | 50 |
| Reference inhibitor | Furafylline | Sulfaphenazole | Tranylcypromine | Quinidine | Ketoconazole |
| Expected signal/noise | 15~25 | 3~5 | 3~5 | 3~6 | 4~15 |
| IC50 (µM) for reference inhibitor | ~1 | ~1 | ~6 | ~0.01 | ~0.06 |

CEC = 3-Cyano-7-ethoxy-coumarin
MFC = 7-methoxy-4-trifluoromethyl-coumarin
MAMC = 7-methoxy-4-(aminomethyl)-coumarin
BFC = 7-bensyloxy-4-trifluoromethyl-coumarin Summary of Biological Data
In Vitro Pharmacology A summary of the in vitro primary pharmacology data for (R)-3-((E)-2-(pyrrolidin-3-yl)vinyl)-5-(tetrahydropyran-4-yloxy)pyridine or a salt thereof is presented in Table 3 and discussed in detail below.

Primary pharmacology and selectivity: The capacity of (R)-3-((E)-2-(pyrrolidin-3-yl)vinyl)-5-(tetrahydropyran-4-yloxy)pyridine or a salt thereof to bind to α4β2 receptors was determined with receptor binding inhibition assays using human recombinant α4β2 receptors expressed in SH-EP1 cellular membranes and rat native α4β2 receptors in rat cortical membranes.

(R)-3-((E)-2-(Pyrrolidin-3-yl)vinyl)-5-(tetrahydropyran-4-yloxy)pyridine or a salt thereof inhibited the binding of [$^3$H]-nicotine to human recombinant α4β2 nicotinic receptors with a $K_i$ of 2 nM and [$^3$H]epibatidine to rat native α4β2 receptors with a $K_i$ of 4 nM.

(R)-3-((E)-2-(Pyrrolidin-3-yl)vinyl)-5-(tetrahydropyran-4-yloxy)pyridine or a salt thereof inhibited the binding of [$^3$H]methyllycaconitine (MLA) to rat native α7 receptors in rat hippocampal membranes with a $K_i$ of >10000 nM. (R)-3-((E)-2-(Pyrrolidin-3-yl)vinyl)-5-(tetrahydropyran-4-yloxy)pyridine or a salt thereof also displayed reduced affinity for human native ganglion-type nicotinic receptors (likely α3β4), inhibiting the binding of [$^3$H]epibatidine to receptors in SH-SY5Y membranes with a $K_i$ of 3400 nM, and reduced affinity for human native muscle-type nicotinic receptors (likely α1β1γδ), inhibiting the binding of [$^3$H]epibatidine to receptors in TE-671 membranes with a $K_i$ of 25000 nM.

TABLE 3

Summary of (R)-3-(2-(pyrrolidin-3-yl)vinyl)-5-((tetrahydro-2H-pyran-4 yl)oxy)pyridine, or a salt thereof, in vitro pharmacology
Target affinity and activation

| | |
|---|---|
| Rat cortex binding $K_i$ | 4 nM |
| Human recombinant (SH-EP 1) α4β2 binding $K_i$ | 2 nM |
| Rat hippocampus (α7, $K_i$) | >10000 nM |
| Human ganglionic (SH-SY5Y), $K_i$ | 3400 nM |
| Human (TE671/RD) muscle, $K_i$ | 25 μM |
| Human recombinant (SH-EP 1) α4β2 $EC_{50}$, Emax (Ca flux) | 0.1 μM, 76% |
| Human ganglionic (SH-SY5Y), $EC_{50}$, Emax (Ca flux) | 11 μM, 13% |
| Human (TE671/RD) muscle, $EC_{50}$, Emax (Ca flux) | 13 μM, 37% |
| Multiple receptor screening assay | Only nicotinic |

Cellular efficacy: The aim of these studies was to determine functional activity of (R)-3-((E)-2-(pyrrolidin-3-yl)vinyl)-5-(tetrahydropyran-4-yloxy)pyridine or a salt thereof at human recombinant α4β2 receptors. (R)-3-((E)-2-(Pyrrolidin-3-yl)vinyl)-5-(tetrahydropyran-4-yloxy)pyridine or a salt thereof is an α4β2 nicotinic agonist activating the receptor with an $EC_{50}$ of 0.1 μM and an $E_{max}$ of 76% in relation to 10 μM nicotine in a calcium flux assay with SH-EP1/human α4β2 cells following 24-h incubation at 29° C.

(R)-3-((E)-2-(Pyrrolidin-3-yl)vinyl)-5-(tetrahydropyran-4-yloxy)pyridine or a salt thereof was tested in ganglion and muscle-type nicotinic receptor ion flux assays to examine functional selectivity. In $Ca^{++}$ efflux assays, (R)-3-((E)-2-(pyrrolidin-3-yl)vinyl)-5-(tetrahydropyran-4-yloxy)pyridine or a salt thereof has an $EC_{50}$ of 11 μM and an $E_{max}$ of 13% at human native ganglion receptors in SH-SY5Y cells, an $EC_{50}$ of 13 μM and an $E_{max}$ of 37% at human native muscle receptors in TE-671 cells.

In Vitro Secondary Pharmacology: Multiple Receptor Screening Assay (R)-3-((E)-2-(Pyrrolidin-3-yl)vinyl)-5-(tetrahydropyran-4-yloxy)pyridine or a salt thereof was tested for selectivity against a panel of 65 receptors. At a single concentration of 10 μM, (R)-3-((E)-2-(pyrrolidin-3-yl)vinyl)-5-(tetrahydropyran-4-yloxy)pyridine or a salt thereof inhibited the binding of labelled ligand only to neuronal nicotinic receptors (α-BnTx insensitive) with 99% inhibition.

Inhibition of hERG

The $IC_{50}$ for the inhibition of hERG (human HEK-239 cells) by (R)-3-((E)-2-pyrrolidin-3-ylvinyl)-5-(tetrahydro-2H-pyran-4-yloxy)pyridine or a salt thereof was determined to be 84 μM.

In Vivo Pharmacology (R)-3-((E)-2-(Pyrrolidin-3-yl)vinyl)-5-(tetrahydropyran-4-yloxy)pyridine or a salt thereof improved long-term visual episodic/declarative memory as assessed by novel object recognition (NOR) task following oral dosing in normal rats. The results of these studies are presented in FIG. 1. The recognition index of the vehicle-treated group 24 h after the acquisition trial was 50±0.5% demonstrating the inability of this group to recognize the familiar object after this delay (left panel). By contrast, animals treated with (R)-3-((E)-2-(pyrrolidin-3-yl)vinyl)-5-(tetrahydropyran-4-yloxy)pyridine or a salt thereof exhibited recognition indexes of 71±2% at the 0.04 μmol/kg dose level and 61±3% and the 1.1 μmol/kg dose level (left panel). In a follow-up NOR study (experimental procedures were identical as used in the first NOR study), the minimum effect dose (MED) level for (R)-3-((E)-2-(pyrrolidin-3-yl)vinyl)-5-(tetrahydropyran-4-yloxy)pyridine or a salt thereof was determined to be 0.004 μmol/kg (right panel) suggesting that the rats are able to recognize the familiar object at all doses levels tested. In the two "recall only" sessions; subset of animals were orally dosed with water on day 1 (i.e., exploratory session) and day 2 (i.e., acquisition session) and then orally dosed either with 1.1 μmol/kg (R)-3-((E)-2-(pyrrolidin-3-yl)vinyl)-5-(tetrahydropyran-4-yloxy)pyridine or a salt thereof (left panel) or 0.04 μmol/kg (right panel) on day 3 (i.e., recall session). Even following a single oral administration, (R)-3-((E)-2-(pyrrolidin-3-yl)vinyl)-5-(tetrahydropyran-4-yloxy)pyridine or a salt thereof demonstrated pro-cognitive effects at these two dose levels. At both dose levels, (R)-3-((E)-2-(pyrrolidin-3-yl)vinyl)-5-(tetrahydropyran-4-yloxy)pyridine or a salt thereof exhibited recognition indexes significantly above controls, indicating recognition of the familiar object following acute dosing. In the Figure, the dashed line at 65% denotes subjective criteria for biological cognitive enhancing activity. *P<0.05.

(R)-3-((E)-2-(Pyrrolidin-3-yl)vinyl)-5-(tetrahydropyran-4-yloxy)pyridine or a salt thereof was evaluated for its duration of effect in the NOR task in normal rats. The results of these studies are presented in FIG. 2. The recognition index of the vehicle-treated group at 0.5 h following dosing on the recall trial was 52±0.8% demonstrating the inability of this group to recognize the familiar object after this delay. By contrast, animals treated with (R)-3-((E)-2-(pyrrolidin-3-yl)vinyl)-5-(tetrahydropyran-4-yloxy)pyridine or a salt thereof (0.004 μmol/kg: oral) exhibited recognition indexes of 72±2% at 0.5 h, 70±3% at 6 h and 70±4% at 8 h suggesting that rats are able to recognize the familiar object for up to 8 h after dosing. In the Figure, the dashed line at 65% denotes subjective criteria for biological cognitive enhancing activity (*P<0.05).

On the basis of these studies, a likely pharmacological effect is possible when dosing (R)-3-((E)-2-(pyrrolidin-3-yl)vinyl)-5-(tetrahydropyran-4-yloxy)pyridine or a salt thereof over a wide range, including relatively low dose levels. One embodiment of the present invention relates to dosing (R)-3-((E)-2-(pyrrolidin-3-yl)vinyl)-5-(tetrahydropyran-4-yloxy)pyridine or a pharmaceutically acceptable salt thereof in oral doses as low as about 0.004 μmol/kg. One embodiment of the present invention relates to an oral dose of less than 100 mg, preferably less than 50 mg, more preferably less than 10 mg, and most preferably less than 1 mg. These effective doses typically represent the amount administered as a single dose, or as one or more doses administered over a 24 h period.

Radial Arm Maze (RAM) Studies

Figure 3:
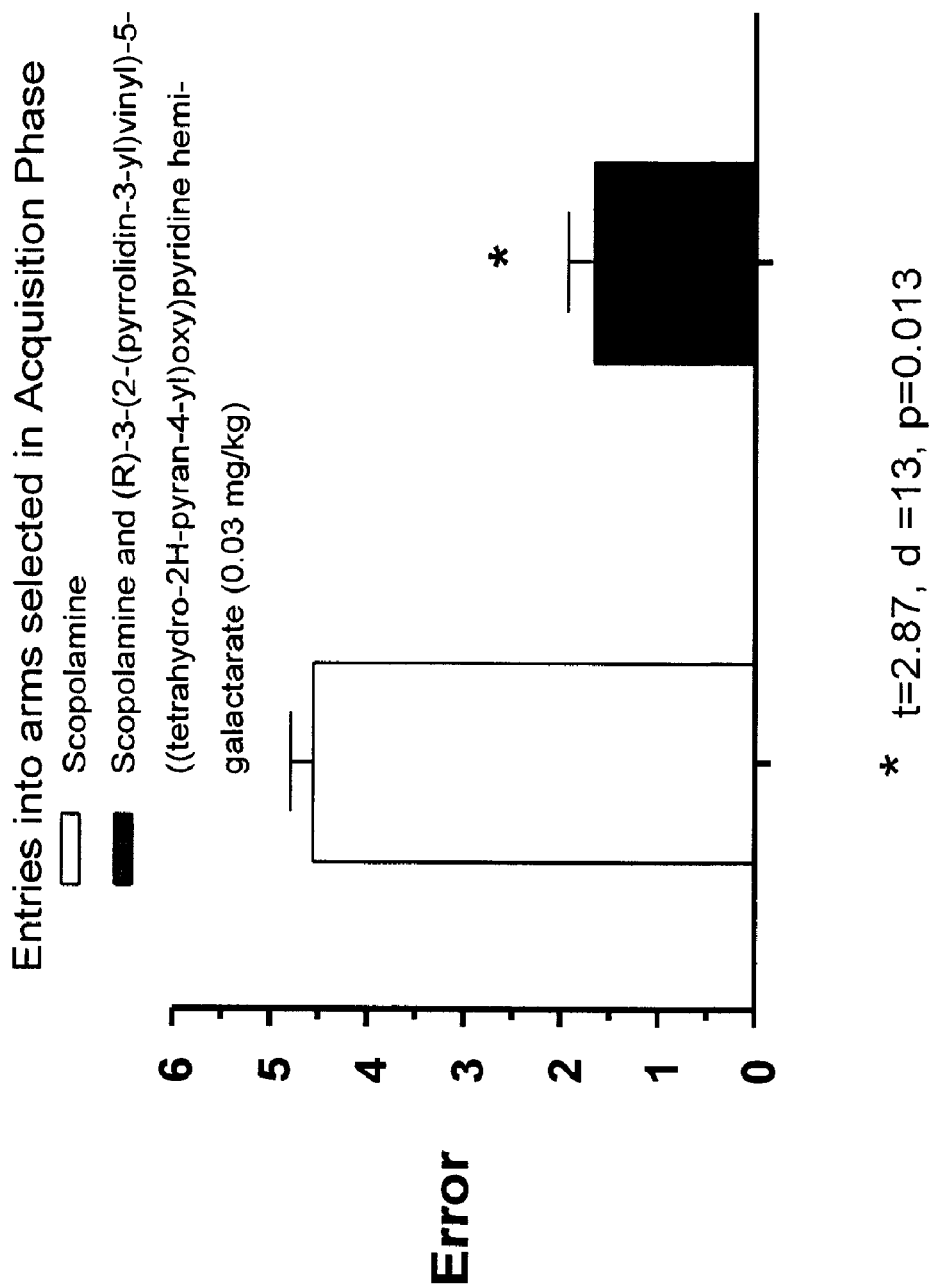
FIG. 3 depicts results of Radial Arm Maze (RAM) Studies in which (R)-3-((E)-2-(pyrrolidin-3-yl)vinyl)-5-(tetrahydropyran-4-yloxy)pyridine or a salt thereof, Compound A, overcomes scopolamine induced deficits in the radial arm maze.

In a second cognitive assay, (R)-3-((E)-2-(pyrrolidin-3-yl)vinyl)-5-(tetrahydropyran-4-yloxy)pyridine or a salt thereof attenuated cognitive deficits, induced by scopolamine, in an animal model of working memory. Results of these experiments are illustrated in FIG. 3. During the acquisition trial, rats were allowed access to 7 of the eight arms whereas, in the test trial, all 8 arms were available, however, only the first visit to the previously blocked arm (i.e., the arm that was blocked during the acquisition trial) was reinforced. Scopolamine (0.3±0.1 mg/kg; s.c.) was administered 0.5 h prior to the acquisition trial, and (R)-3-((E)-2-(pyrrolidin-3-yl)vinyl)-5-(tetrahydropyran-4-yloxy)pyridine or a salt thereof (0.03 mg/kg or 0.1 μmol/kg; p.o.) was administered 0.5 h prior to the test trial. (R)-3-((E)-2-(Pyrrolidin-3-yl)vinyl)-5-(tetrahydropyran-4-yloxy)pyridine or a salt thereof was able to reverse scopolamine-induced cognitive deficits (*P<0.05).

Human Cytochrome P450 (CYP) Inhibition, Induction, Transport, and Drug-Drug Interaction Potential A CYP450 inhibition assay using fluorescent substrates and recombinant enzymes showed no evidence of inhibition by (R)-3-((E)-2-(pyrrolidin-3-yl)vinyl)-5-(tetrahydropyran-4-yloxy)pyridine or a salt thereof of the 5 major CYPs ($IC_{50}$>20 μM, Table 4). In addition, no evidence of time-dependent inhibition of CYP3A4, CYP2D6, CYP2B6, CYP2C9, or CYP1A2 was observed. No PXR (pregnane X receptor) activation by (R)-3-((E)-2-(pyrrolidin-3-yl)vinyl)-5-(tetrahydropyran-4-yloxy)pyridine was observed up to 10 μM, thus the risk related to induction of P450s is believed to be negligible.

TABLE 4

| CYP inhibition $IC_{50}$ (μM) | |
|---|---|
| CYP mediated metabolism | |
| 1A2 | >20 |
| 3A4 | >20 |
| 2C9 | >20 |
| 2C19 | >20 |
| 2D6 | >20 |

(R)-3-((E)-2-(Pyrrolidin-3-yl)vinyl)-5-(tetrahydropyran-4-yloxy)pyridine or a salt thereof exhibits low hepatic turnover rate in human liver microsomes or hepatocytes. Preliminary phenotyping data suggested that both CYP2D6 and FMO3 contributed to the metabolism of (R)-3-((E)-2-(pyrrolidin-3-yl)vinyl)-5-(tetrahydropyran-4-yloxy)pyridine or a salt thereof. In addition, renal clearance was expected to be the major elimination route, contributing more than 50% of the total clearance in human. Therefore any variation of (R)-3-((E)-2-(pyrrolidin-3-yl)vinyl)-5-(tetrahydropyran-4-yloxy)pyridine or a salt thereof metabolism in human due to CYP polymorphism is expected to be less than 2 fold due to the significant renal clearance and low hepatic clearance.

Test compounds for the experiments described herein were employed in free or salt form, and, if not otherwise stated, the test compound is (R)-3-((E)-2-(pyrrolidin-3-yl)vinyl)-5-(tetrahydropyran-4-yloxy)pyridine hemigalactarate.

The specific pharmacological responses observed may vary according to and depending on the particular active compound selected or whether there are present pharmaceutical carriers, as well as the type of pharmaceutical composition and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation. Modifications will be obvious to those skilled in the art, and all modifications that do not depart from the spirit of the invention are intended to be included with the scope of the appended claims.

What is claimed is:

1. A compound diethyl (R)-2-(1-(tert-butoxycarbonyl)pyrrolidin-3-yl)malonate.

2. A compound (R)-2-(1-(tert-butoxycarbonyl)pyrrolidin-3-yl)malonic acid.

3. A compound tert-butyl (R)-3-(2-hydroxyethyl)pyrrolidine-1-carboxylate.

4. A compound tert-butyl (R)-3-(2-iodoethyl)pyrrolidine-1-carboxylate.

5. A method of making tert-butyl (R)-3-vinylpyrrolidine-1-carboxylate through the intermediacy of one or more of diethyl (R)-2-(1-(tert-butoxycarbonyl)pyrrolidin-3-yl)malonate, (R)-2-(1-(tert-butoxycarbonyl)pyrrolidin-3-yl)malonic acid, tert-butyl (R)-3-(2-hydroxyethyl)pyrrolidine-1-carboxylate, and tert-butyl (R)-3-(2-iodoethyl)pyrrolidine-1-carboxylate.

* * * * *